(12) United States Patent
Morandi et al.

(10) Patent No.: US 12,344,898 B2
(45) Date of Patent: Jul. 1, 2025

(54) METHOD FOR DETERMINING A HEAD AND NECK SQUAMOUS CELL CARCINOMA

(71) Applicant: ALMA MATER STUDIORUM—Universita' di Bologna, Bologna (IT)

(72) Inventors: Luca Morandi, Bologna (IT); Davide Bartolomeo Gissi, Bologna (IT); Achille Tarsitano, Bologna (IT)

(73) Assignee: ALMA MATER STUDIORUM—Universita' di Bologna, Bologna (IT)

( * ) Notice: Subject to any disclaimer, the term of this patent is extended or adjusted under 35 U.S.C. 154(b) by 727 days.

(21) Appl. No.: 16/347,387

(22) PCT Filed: Nov. 3, 2017

(86) PCT No.: PCT/IB2017/056875
§ 371 (c)(1),
(2) Date: May 3, 2019

(87) PCT Pub. No.: WO2018/083646
PCT Pub. Date: May 11, 2018

(65) Prior Publication Data
US 2020/0299773 A1    Sep. 24, 2020

(30) Foreign Application Priority Data
Nov. 4, 2016    (IT) .......................... 102016000111174

(51) Int. Cl.
*C12Q 1/6886* (2018.01)

(52) U.S. Cl.
CPC ..... *C12Q 1/6886* (2013.01); *C12Q 2523/125* (2013.01); *C12Q 2525/155* (2013.01); *C12Q 2525/179* (2013.01); *C12Q 2525/191* (2013.01); *C12Q 2535/122* (2013.01); *C12Q 2537/143* (2013.01); *C12Q 2600/118* (2013.01); *C12Q 2600/154* (2013.01); *G01N 2800/52* (2013.01); *G01N 2800/7028* (2013.01)

(58) Field of Classification Search
CPC ............ C12Q 1/6886; C12Q 2523/125; C12Q 2525/155; C12Q 2525/179; C12Q 2525/191; C12Q 2535/122; C12Q 2537/143; C12Q 2600/118; C12Q 2600/154
See application file for complete search history.

(56) References Cited

U.S. PATENT DOCUMENTS

2008/0057590 A1* 3/2008 Urdea ................ G01N 33/6845
436/71
2011/0300536 A1    12/2011 Li et al.

FOREIGN PATENT DOCUMENTS

WO    2011112880 A2    9/2011

OTHER PUBLICATIONS

Hu et al. BMC Bioinformatics 2015; 16: 220; DOI 10.1186/s12859-015-0649-2 (Year: 2015).*
Guo et al. BMC Genomics 2013; 14: 774; doi: 10.1186/1471-2164-14-774. (Year: 2013).*
Hernández et al. BioTechniques 2013; 55: 181-197. (Year: 2013).*
Lee et al. Cancer Letters 2013; 340: 171-178. (Year: 2013).*
Warnecke et al. Methods 2002; 27: 101-107. (Year: 2002).*
Ehrich et al. Nucleic Acids Research 2007; 35: e29. (Year: 2007).*
Cronn et al. American Journal of Botany 2012; 99: 291-311. (Year: 2012).*
Hadd et al. The Journal of Molecular Diagnostics 2013; 15: 234-247. (Year: 2013).*
Ergüner et al. Annual International Conference of the IEEE Engineering in Medicine and Biology Society 2015; 6453-6456. (Year: 2015).*
Morandi et al. Clinical Epigenetics 2017; 9: 85 (Year: 2017).*
Gissi et al. International Journal of Molecular Sciences 2020; 21: 6691 (Year: 2020).*
Morandi et al. Journal of Cranio-Maxillo-Facial Surgery 2015; 43: 1494-1500 (Year: 2015).*
Qureshi et al. International Journal of Surgery 2010; 8: 194-198 (Year: 2010).*
Gissi et al. 13-gene DNA Methylation Analysis from Oral Brushing: A Promising Non Invasive Tool in the Follow-up of Oral Cancer Patients. Journal of Clinical Medicine 2019; 8: 2107; doi:10.3390/jcm8122107. (Year: 2019).*
Demokan, S., et al., "KIF1A and EDNRB are differentially methylated in primary HNSCC and salivary rinses", International Journal of Cancer, vol. 127, No. 10, Nov. 15, 2010, pp. 2351-2359.
Jithesh P.V., et al., "The epigenetic landscape of oral squamous cell carcinoma", British Journal of Cancer, vol. 108, No. 2, Jan. 3, 2013, pp. 370-379.
Khor, G.H., et al., "DNA methylation profiling revealed promoter hypermethylation-induced silencing of p16, DDAH2 and DUSP1 in primary oral squamous cell carcinoma", International Journal of Medical Sciences, vol. 10, No. 12, Jan. 1, 2013, pp. 1727-1739.
Search Report and Written Opinion of PCT/IB2017/056875 of May 3, 2018.

* cited by examiner

*Primary Examiner* — Samuel C Woolwine
(74) *Attorney, Agent, or Firm* — Silvia Salvadori, P.C.; Silvia Salvadori

(57) ABSTRACT

The present invention refers to a method performed in vitro to determine a Head and Neck Squamous Cell Carcinoma, preferably at early stage, based on the measuring of the hypermethylation and/or hypomethylation level(s) of CpG islands of specific set of genes.

Figure 2B:
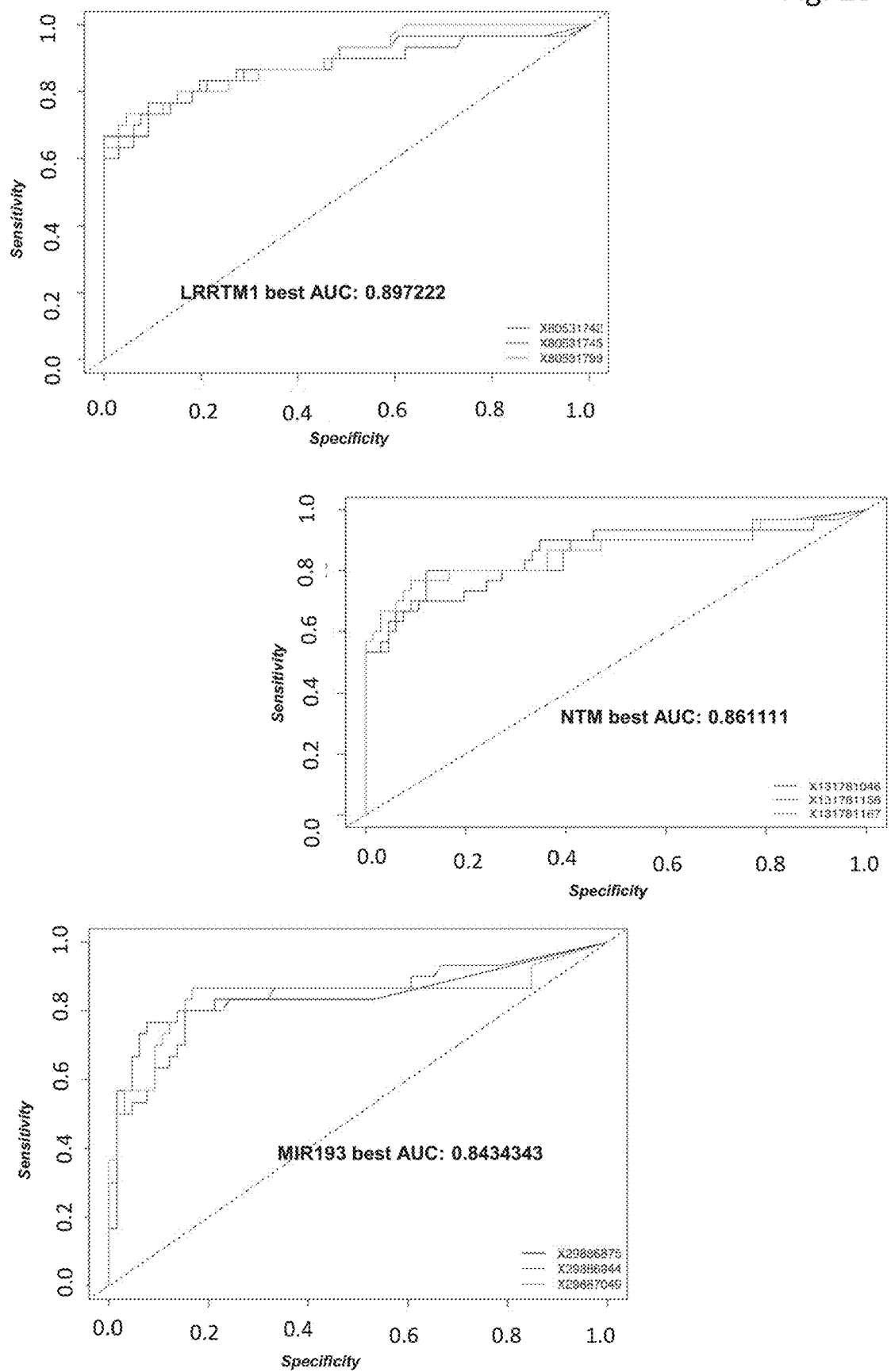

14 Claims, 13 Drawing Sheets
Specification includes a Sequence Listing.

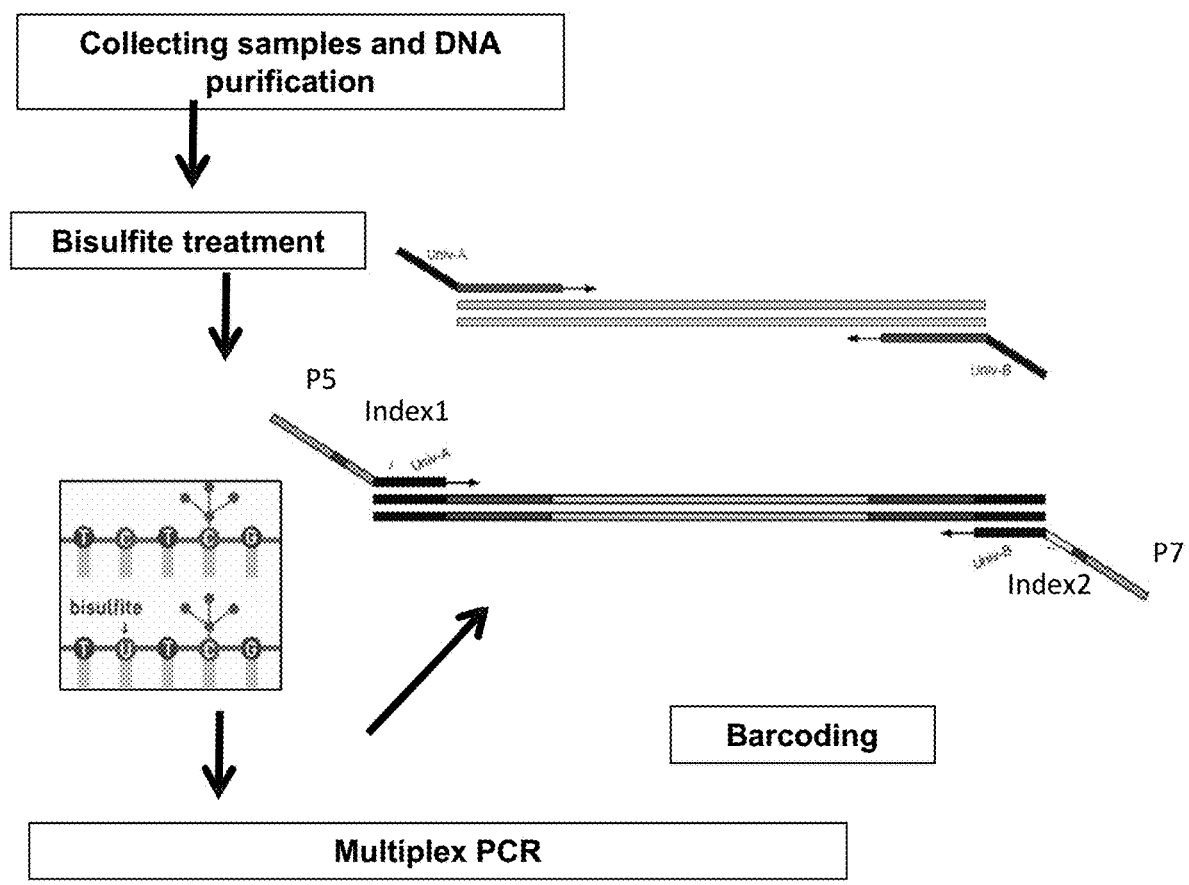
Fig. 1-A

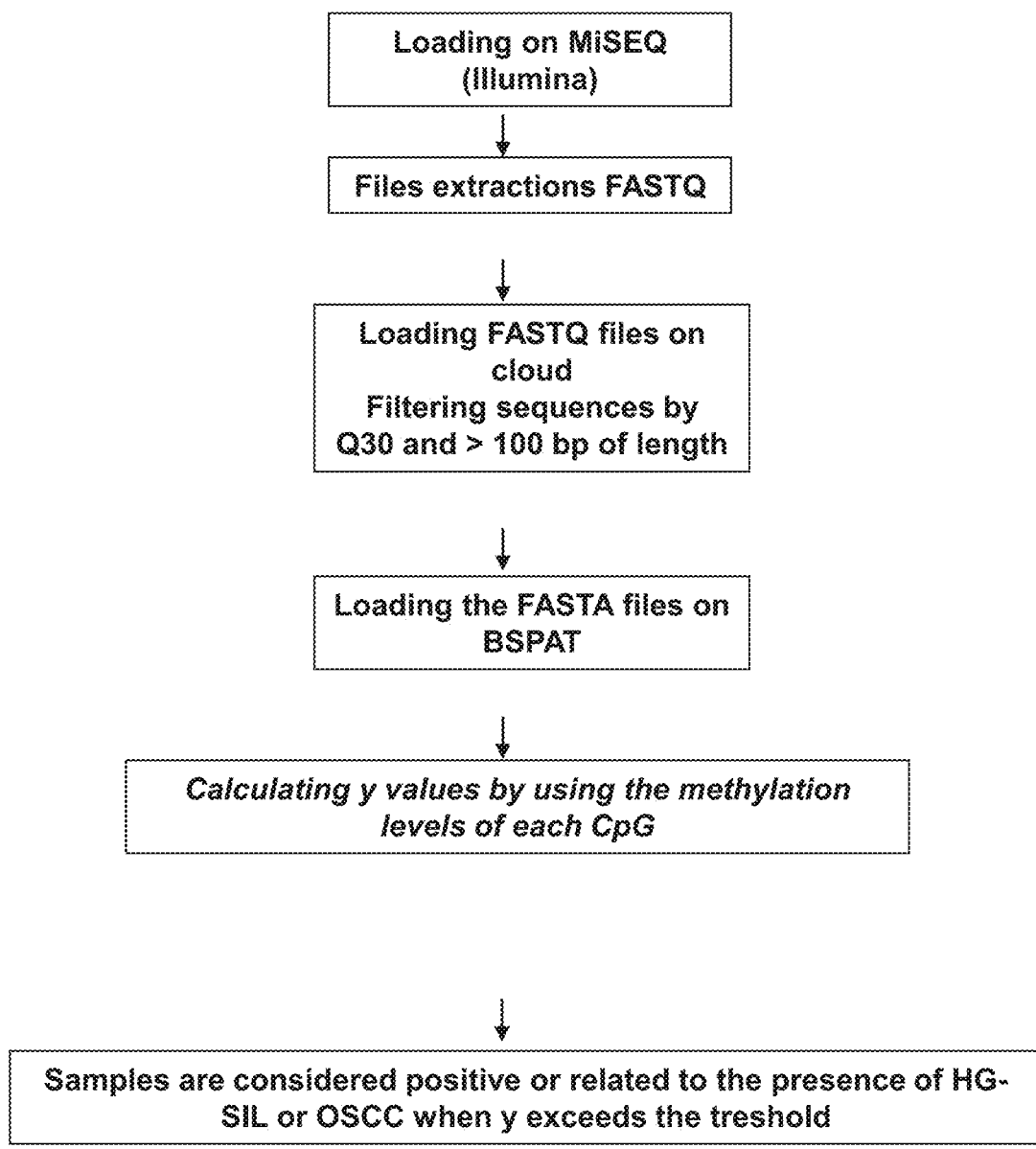
Fig. 1-B

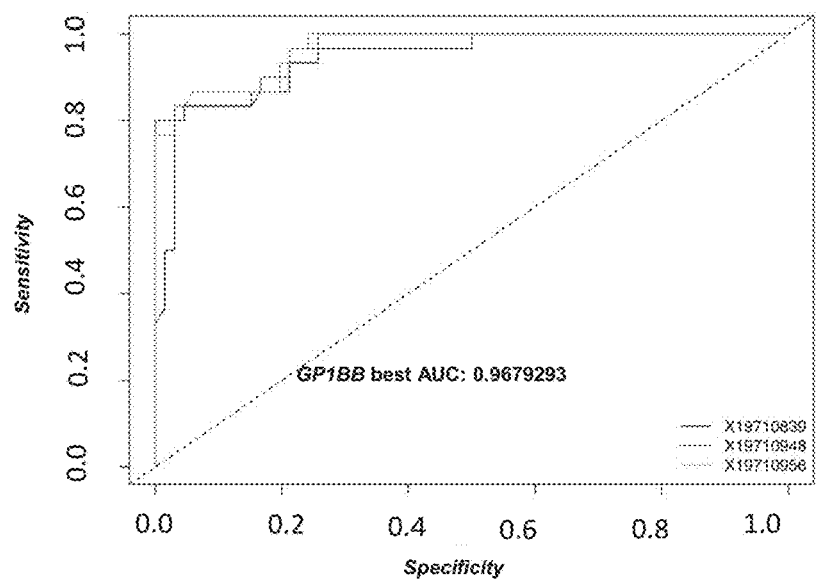
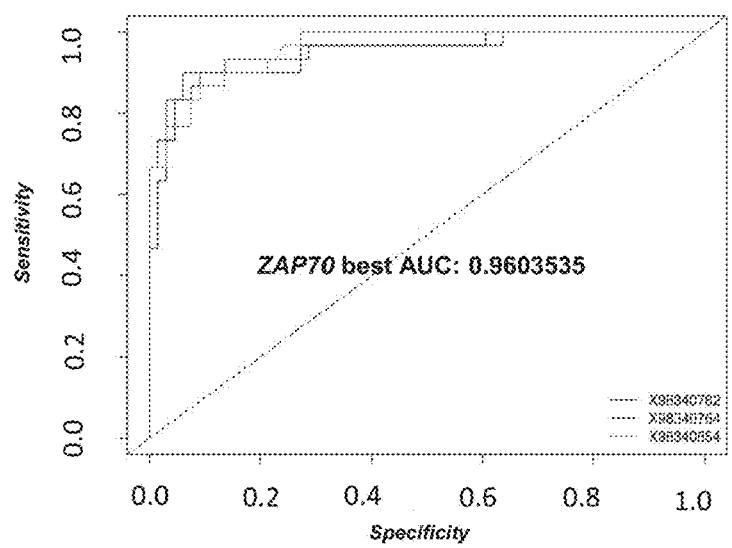
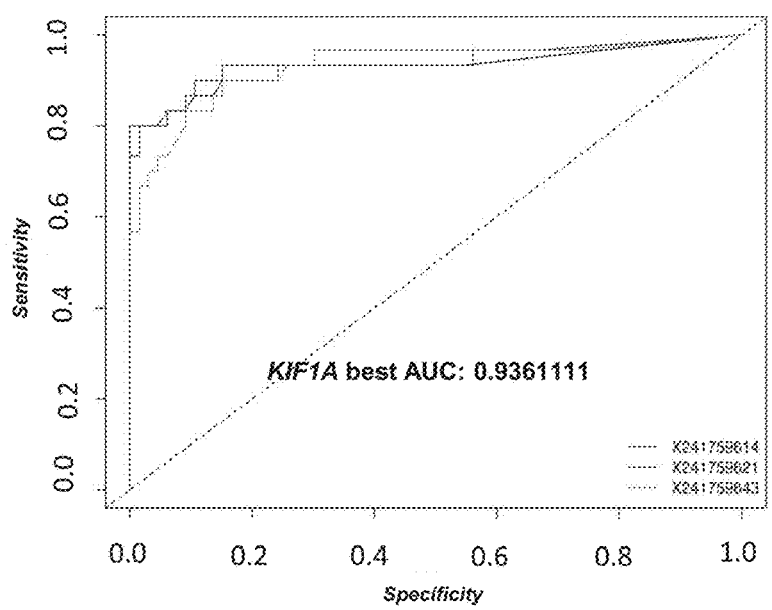
Fig. 2A

Fig. 3D
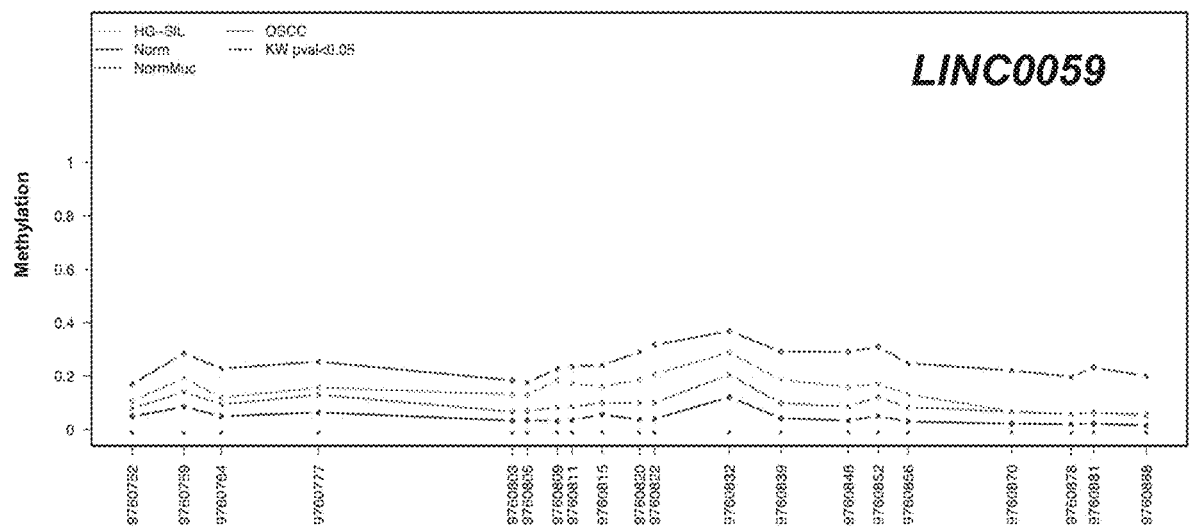
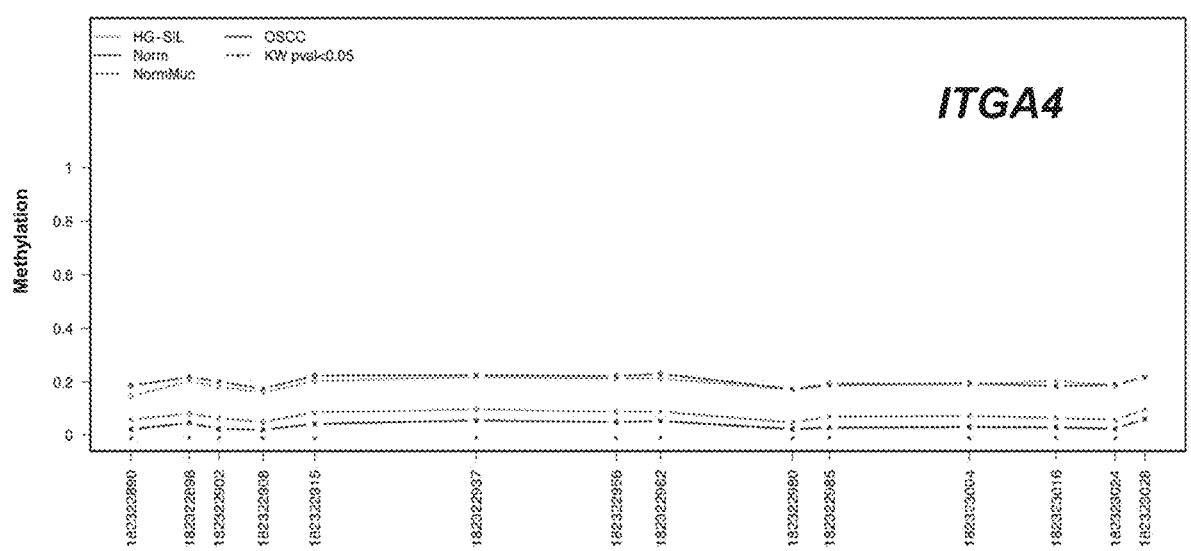

Fig. 3D
Cont.
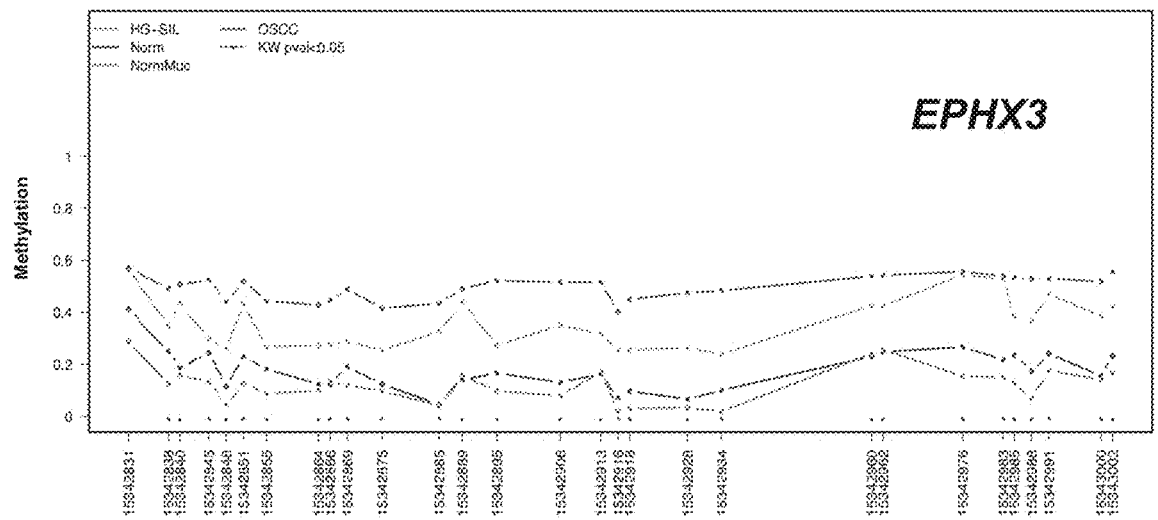
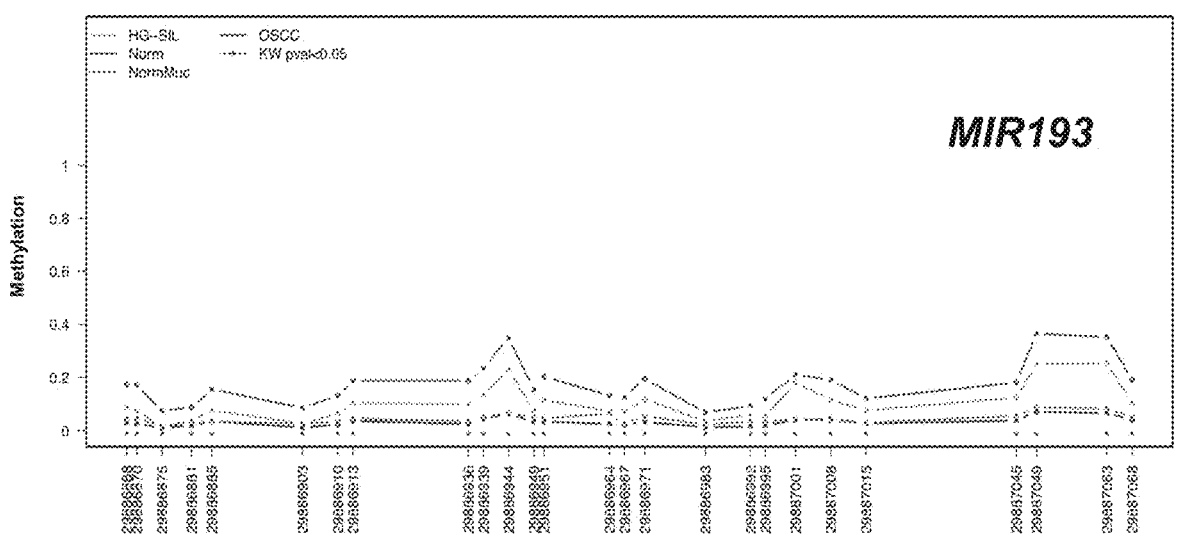

SEQUENCE LISTING

<160> NUMBER OF SEQ ID NOS: 75

<210> SEQ ID NO 1
<211> LENGTH: 39
<212> TYPE: DNA
<213> ORGANISM: Artificial Sequence
<220> FEATURE:
<223> OTHER INFORMATION: PARP15-forward

<400> SEQUENCE: 1
gtaatacgac ggtcagtgtt gttttgagtt tagggggttt                                 39

<210> SEQ ID NO 2
<211> LENGTH: 40
<212> TYPE: DNA
<213> ORGANISM: Artificial Sequence
<220> FEATURE:
<223> OTHER INFORMATION: PARP15-reverse

<400> SEQUENCE: 2
caggaaacag ctatgacact caaccctact atccccttcc                                 40

<210> SEQ ID NO 3
<211> LENGTH: 38
<212> TYPE: DNA
<213> ORGANISM: Artificial Sequence
<220> FEATURE:
<223> OTHER INFORMATION: ITGA4-forward

<400> SEQUENCE: 3
gtaatacgac ggtcagtgag agygtatggt ttgggaag                                   38

<210> SEQ ID NO 4
<211> LENGTH: 39
<212> TYPE: DNA
<213> ORGANISM: Artificial Sequence
<220> FEATURE:
<223> OTHER INFORMATION: ITGA4-reverse

<400> SEQUENCE: 4
caggaaacag ctatgacaaa aacrcatcaa tccaactct                                  39

<210> SEQ ID NO 5
<211> LENGTH: 36
<212> TYPE: DNA
<213> ORGANISM: Artificial Sequence
<220> FEATURE:
<223> OTHER INFORMATION: NMT-forward

<400> SEQUENCE: 5
gtaatacgac ggtcagtgtg tttgaattgt ygttgg                                     36

<210> SEQ ID NO 6
<211> LENGTH: 37
<212> TYPE: DNA
<213> ORGANISM: Artificial Sequence
<220> FEATURE:
<223> OTHER INFORMATION: NMT-reverse

<400> SEQUENCE: 6
caggaaacag ctatgacata ttcctccccc aaatcca                                    37

<210> SEQ ID NO 7
<211> LENGTH: 40
<212> TYPE: DNA
<213> ORGANISM: Artificial Sequence
<220> FEATURE:
<223> OTHER INFORMATION: ZAP70-forward

<400> SEQUENCE: 7
gtaatacgac ggtcagttat tgtggatygg tagagttttg          40

<210> SEQ ID NO 8
<211> LENGTH: 36
<212> TYPE: DNA
<213> ORGANISM: Artificial Sequence
<220> FEATURE:
<223> OTHER INFORMATION: ZAP70-reverse

<400> SEQUENCE: 8
caggaaacag ctatgacctc tcacctccaa cttcca          36

<210> SEQ ID NO 9
<211> LENGTH: 40
<212> TYPE: DNA
<213> ORGANISM: Artificial Sequence
<220> FEATURE:
<223> OTHER INFORMATION: MIR193A-forward

<400> SEQUENCE: 9
gtaatacgac ggtcagtgtg taattttttgg agggttgggt          40

<210> SEQ ID NO 10
<211> LENGTH: 46
<212> TYPE: DNA
<213> ORGANISM: Artificial Sequence
<220> FEATURE:
<223> OTHER INFORMATION: MIR193A-reverse

<400> SEQUENCE: 10
caggaaacag ctatgacaaa ctaaaacttt ataaaccaat taatcc          46

<210> SEQ ID NO 11
<211> LENGTH: 37
<212> TYPE: DNA
<213> ORGANISM: Artificial Sequence
<220> FEATURE:
<223> OTHER INFORMATION: EPHX3-forward

<400> SEQUENCE: 11
gtaatacgac ggtcagtggy gatatgtygg agttggt          37

<210> SEQ ID NO 12
<211> LENGTH: 37
<212> TYPE: DNA
<213> ORGANISM: Artificial Sequence
<220> FEATURE:
<223> OTHER INFORMATION: EPHX3-reverse

<400> SEQUENCE: 12
caggaaacag ctatgaccca acraaaaatc rctcaaa          37

<210> SEQ ID NO 13
<211> LENGTH: 41
<212> TYPE: DNA
<213> ORGANISM: Artificial Sequence
<220> FEATURE:
<223> OTHER INFORMATION: KIF1A-forward

<400> SEQUENCE: 13
gtaatacgac ggtcagtata aattagttgg ygattggagt t          41

<210> SEQ ID NO 14
<211> LENGTH: 40
<212> TYPE: DNA
<213> ORGANISM: Artificial Sequence
<220> FEATURE:
<223> OTHER INFORMATION: KIF1A-reverse

<400> SEQUENCE: 14
caggaaacag ctatgacccc crcataaaca ctaacataaa          40

<210> SEQ ID NO 15
<211> LENGTH: 42
<212> TYPE: DNA
<213> ORGANISM: Artificial Sequence
<220> FEATURE:
<223> OTHER INFORMATION: LINC00599-forward

<400> SEQUENCE: 15
gtaatacgac ggtcagtgtt aagaatgggg ttggttgagt at        42

<210> SEQ ID NO 16
<211> LENGTH: 44
<212> TYPE: DNA
<213> ORGANISM: Artificial Sequence
<220> FEATURE:
<223> OTHER INFORMATION: LINC00599-reverse

<400> SEQUENCE: 16
caggaaacag ctatgacccc tatctatcac aaactacaca cctc      44

<210> SEQ ID NO 17
<211> LENGTH: 36
<212> TYPE: DNA
<213> ORGANISM: Artificial Sequence
<220> FEATURE:
<223> OTHER INFORMATION: FLI1-forward

<400> SEQUENCE: 17
gtaatacgac ggtcagtata ggggagtgag ggtagg               36

<210> SEQ ID NO 18
<211> LENGTH: 36
<212> TYPE: DNA
<213> ORGANISM: Artificial Sequence
<220> FEATURE:
<223> OTHER INFORMATION: FLI1-reverse

<400> SEQUENCE: 18
caggaaacag ctatgacccc rccrcttacc ttaata               36

<210> SEQ ID NO 19
<211> LENGTH: 42
<212> TYPE: DNA
<213> ORGANISM: Artificial Sequence
<220> FEATURE:
<223> OTHER INFORMATION: GP1BB-forward

<400> SEQUENCE: 19
gtaatacgac ggtcagtttg ttttggtgat aggagaataa tg        42

<210> SEQ ID NO 20
<211> LENGTH: 42
<212> TYPE: DNA
<213> ORGANISM: Artificial Sequence
<220> FEATURE:
<223> OTHER INFORMATION: GP1BB-reverse

<400> SEQUENCE: 20
caggaaacag ctatgacacc taaccaaaaa taacccaaaa ac					42

<210> SEQ ID NO 21
<211> LENGTH: 36
<212> TYPE: DNA
<213> ORGANISM: Artificial Sequence
<220> FEATURE:
<223> OTHER INFORMATION: MIR296-forward

<400> SEQUENCE: 21
gtaatacgac ggtcagtggg tattggggaa tggtga					36

<210> SEQ ID NO 22
<211> LENGTH: 37
<212> TYPE: DNA
<213> ORGANISM: Artificial Sequence
<220> FEATURE:
<223> OTHER INFORMATION: MIR296-reverse

<400> SEQUENCE: 22
caggaaacag ctatgaccra aaaccccaaa cctaaca					37

<210> SEQ ID NO 23
<211> LENGTH: 37
<212> TYPE: DNA
<213> ORGANISM: Artificial Sequence
<220> FEATURE:
<223> OTHER INFORMATION: LRRTM1-forward

<400> SEQUENCE: 23
gtaatacgac ggtcagtgtt tggtggaggg aaggagt					37

<210> SEQ ID NO 24
<211> LENGTH: 37
<212> TYPE: DNA
<213> ORGANISM: Artificial Sequence
<220> FEATURE:
<223> OTHER INFORMATION: LRRTM1-reverse

<400> SEQUENCE: 24
caggaaacag ctatgactaa ccracrccac cttttac					37

<210> SEQ ID NO 25
<211> LENGTH: 43
<212> TYPE: DNA
<213> ORGANISM: Artificial Sequence
<220> FEATURE:
<223> OTHER INFORMATION: hTERT-forward

<400> SEQUENCE: 25
gtaatacgac ggtcagtggt ttttgtattt tatttttgtg gtt					43

<210> SEQ ID NO 26
<211> LENGTH: 41
<212> TYPE: DNA
<213> ORGANISM: Artificial Sequence
<220> FEATURE:
<223> OTHER INFORMATION: hTERT-reverse

<400> SEQUENCE: 26
caggaaacag ctatgaccca acttcctcaa accctattta a					41

<210> SEQ ID NO 27

```
<211> LENGTH: 59
<212> TYPE: DNA
<213> ORGANISM: Artificial Sequence
<220> FEATURE:
<223> OTHER INFORMATION: PARP15-forward
<220> FEATURE:
<221> NAME/KEY: misc_feature
<222> LOCATION: (34)..(37)
<223> OTHER INFORMATION: n is a, c, g, or t

<400> SEQUENCE: 27
tcgtcggcag cgtcagatgt gtataagaga cagnnnngtt gttttgagtt tagggttt      59

<210> SEQ ID NO 28
<211> LENGTH: 61
<212> TYPE: DNA
<213> ORGANISM: Artificial Sequence
<220> FEATURE:
<223> OTHER INFORMATION: PARP15-reverse
<220> FEATURE:
<221> NAME/KEY: misc_feature
<222> LOCATION: (35)..(38)
<223> OTHER INFORMATION: n is a, c, g, or t

<400> SEQUENCE: 28
gtctcgtggg ctcggagatg tgtataagag acagnnnnac tcaaccctac tatcccttc     60 c                                                                    61

<210> SEQ ID NO 29
<211> LENGTH: 58
<212> TYPE: DNA
<213> ORGANISM: Artificial Sequence
<220> FEATURE:
<223> OTHER INFORMATION: ITGA4-forward
<220> FEATURE:
<221> NAME/KEY: misc_feature
<222> LOCATION: (34)..(37)
<223> OTHER INFORMATION: n is a, c, g, or t

<400> SEQUENCE: 29
tcgtcggcag cgtcagatgt gtataagaga cagnnnngag agygtatggt ttgggaag      58

<210> SEQ ID NO 30
<211> LENGTH: 60
<212> TYPE: DNA
<213> ORGANISM: Artificial Sequence
<220> FEATURE:
<223> OTHER INFORMATION: ITGA4-reverse
<220> FEATURE:
<221> NAME/KEY: misc_feature
<222> LOCATION: (35)..(38)
<223> OTHER INFORMATION: n is a, c, g, or t

<400> SEQUENCE: 30
gtctcgtggg ctcggagatg tgtataagag acagnnnnaa aaacrcatca atccaactct    60

<210> SEQ ID NO 31
<211> LENGTH: 56
<212> TYPE: DNA
<213> ORGANISM: Artificial Sequence
<220> FEATURE:
<223> OTHER INFORMATION: NMT-forward
<220> FEATURE:
<221> NAME/KEY: misc_feature
<222> LOCATION: (34)..(37)
<223> OTHER INFORMATION: n is a, c, g, or t

<400> SEQUENCE: 31
tcgtcggcag cgtcagatgt gtataagaga cagnnnngtg tttgaattgt ygttgg        56
```

<210> SEQ ID NO 32
<211> LENGTH: 58
<212> TYPE: DNA
<213> ORGANISM: Artificial Sequence
<220> FEATURE:
<223> OTHER INFORMATION: NMT-reverse
<220> FEATURE:
<221> NAME/KEY: misc_feature
<222> LOCATION: (35)..(38)
<223> OTHER INFORMATION: n is a, c, g, or t

<400> SEQUENCE: 32
gtctcgtggg ctcggagatg tgtataagag acagnnnnat attcctcccc caaatcca        58

<210> SEQ ID NO 33
<211> LENGTH: 60
<212> TYPE: DNA
<213> ORGANISM: Artificial Sequence
<220> FEATURE:
<223> OTHER INFORMATION: ZAP70-forward
<220> FEATURE:
<221> NAME/KEY: misc_feature
<222> LOCATION: (34)..(37)
<223> OTHER INFORMATION: n is a, c, g, or t

<400> SEQUENCE: 33
tcgtcggcag cgtcagatgt gtataagaga cagnnnntat tgtggatygg tagagttttg        60

<210> SEQ ID NO 34
<211> LENGTH: 57
<212> TYPE: DNA
<213> ORGANISM: Artificial Sequence
<220> FEATURE:
<223> OTHER INFORMATION: ZAP70-reverse
<220> FEATURE:
<221> NAME/KEY: misc_feature
<222> LOCATION: (35)..(38)
<223> OTHER INFORMATION: n is a, c, g, or t

<400> SEQUENCE: 34
gtctcgtggg ctcggagatg tgtataagag acagnnnnct ctcacctcca acttcca        57

<210> SEQ ID NO 35
<211> LENGTH: 60
<212> TYPE: DNA
<213> ORGANISM: Artificial Sequence
<220> FEATURE:
<223> OTHER INFORMATION: MIR193A-forward
<220> FEATURE:
<221> NAME/KEY: misc_feature
<222> LOCATION: (34)..(37)
<223> OTHER INFORMATION: n is a, c, g, or t

<400> SEQUENCE: 35
tcgtcggcag cgtcagatgt gtataagaga cagnnnngtg taattttggg agggttgggt        60

<210> SEQ ID NO 36
<211> LENGTH: 67
<212> TYPE: DNA
<213> ORGANISM: Artificial Sequence
<220> FEATURE:
<223> OTHER INFORMATION: MIR193A-reverse
<220> FEATURE:
<221> NAME/KEY: misc_feature
<222> LOCATION: (35)..(38)
<223> OTHER INFORMATION: n is a, c, g, or t

<400> SEQUENCE: 36

```
gtctcgtggg ctcggagatg tgtataagag acagnnnnaa actaaaactt tataaaccaa    60
ttaatcc                                                              67
```

<210> SEQ ID NO 37
<211> LENGTH: 57
<212> TYPE: DNA
<213> ORGANISM: Artificial Sequence
<220> FEATURE:
<223> OTHER INFORMATION: EPHX3-forward
<220> FEATURE:
<221> NAME/KEY: misc_feature
<222> LOCATION: (34)..(37)
<223> OTHER INFORMATION: n is a, c, g, or t

<400> SEQUENCE: 37

```
tcgtcggcag cgtcagatgt gtataagaga cagnnnnggy gatatgtygg agttggt       57
```

<210> SEQ ID NO 38
<211> LENGTH: 58
<212> TYPE: DNA
<213> ORGANISM: Artificial Sequence
<220> FEATURE:
<223> OTHER INFORMATION: EPHX3-reverse
<220> FEATURE:
<221> NAME/KEY: misc_feature
<222> LOCATION: (35)..(38)
<223> OTHER INFORMATION: n is a, c, g, or t

<400> SEQUENCE: 38

```
gtctcgtggg ctcggagatg tgtataagag acagnnnncc aacraaaaat crctcaaa      58
```

<210> SEQ ID NO 39
<211> LENGTH: 61
<212> TYPE: DNA
<213> ORGANISM: Artificial Sequence
<220> FEATURE:
<223> OTHER INFORMATION: KIF1A-forward
<220> FEATURE:
<221> NAME/KEY: misc_feature
<222> LOCATION: (34)..(37)
<223> OTHER INFORMATION: n is a, c, g, or t

<400> SEQUENCE: 39

```
tcgtcggcag cgtcagatgt gtataagaga cagnnnnata aattagttgg ygattggagt    60
t                                                                    61
```

<210> SEQ ID NO 40
<211> LENGTH: 61
<212> TYPE: DNA
<213> ORGANISM: Artificial Sequence
<220> FEATURE:
<223> OTHER INFORMATION: KIF1A-reverse
<220> FEATURE:
<221> NAME/KEY: misc_feature
<222> LOCATION: (35)..(38)
<223> OTHER INFORMATION: n is a, c, g, or t

<400> SEQUENCE: 40

```
gtctcgtggg ctcggagatg tgtataagag acagnnnncc ccrcataaac actaacataa    60
a                                                                    61
```

<210> SEQ ID NO 41
<211> LENGTH: 62
<212> TYPE: DNA
<213> ORGANISM: Artificial Sequence
<220> FEATURE:
<223> OTHER INFORMATION: LINC00599-forward

```
<220> FEATURE:
<221> NAME/KEY: misc_feature
<222> LOCATION: (34)..(37)
<223> OTHER INFORMATION: n is a, c, g, or t

<400> SEQUENCE: 41
tcgtcggcag cgtcagatgt gtataagaga cagnnnngtt aagaatgggg ttggttgagt    60
at                                                                  62

<210> SEQ ID NO 42
<211> LENGTH: 65
<212> TYPE: DNA
<213> ORGANISM: Artificial Sequence
<220> FEATURE:
<223> OTHER INFORMATION: LINC00599-reverse
<220> FEATURE:
<221> NAME/KEY: misc_feature
<222> LOCATION: (35)..(38)
<223> OTHER INFORMATION: n is a, c, g, or t

<400> SEQUENCE: 42
gtctcgtggg ctcggagatg tgtataagag acagnnnncc ctatctatca caaactacac    60
acctc                                                               65

<210> SEQ ID NO 43
<211> LENGTH: 56
<212> TYPE: DNA
<213> ORGANISM: Artificial Sequence
<220> FEATURE:
<223> OTHER INFORMATION: FLI1-forward
<220> FEATURE:
<221> NAME/KEY: misc_feature
<222> LOCATION: (34)..(37)
<223> OTHER INFORMATION: n is a, c, g, or t

<400> SEQUENCE: 43
tcgtcggcag cgtcagatgt gtataagaga cagnnnnata ggggagtgag ggtagg        56

<210> SEQ ID NO 44
<211> LENGTH: 57
<212> TYPE: DNA
<213> ORGANISM: Artificial Sequence
<220> FEATURE:
<223> OTHER INFORMATION: FLI1-reverse
<220> FEATURE:
<221> NAME/KEY: misc_feature
<222> LOCATION: (35)..(38)
<223> OTHER INFORMATION: n is a, c, g, or t

<400> SEQUENCE: 44
gtctcgtggg ctcggagatg tgtataagag acagnnnncc crccrcttac cttaata       57

<210> SEQ ID NO 45
<211> LENGTH: 62
<212> TYPE: DNA
<213> ORGANISM: Artificial Sequence
<220> FEATURE:
<223> OTHER INFORMATION: GP1BB-forward
<220> FEATURE:
<221> NAME/KEY: misc_feature
<222> LOCATION: (34)..(37)
<223> OTHER INFORMATION: n is a, c, g, or t

<400> SEQUENCE: 45
tcgtcggcag cgtcagatgt gtataagaga cagnnnnttg ttttggtgat aggagaataa    60
tg                                                                  62
```

```
<210> SEQ ID NO 46
<211> LENGTH: 63
<212> TYPE: DNA
<213> ORGANISM: Artificial Sequence
<220> FEATURE:
<223> OTHER INFORMATION: GP1BB-reverse
<220> FEATURE:
<221> NAME/KEY: misc_feature
<222> LOCATION: (35)..(38)
<223> OTHER INFORMATION: n is a, c, g, or t

<400> SEQUENCE: 46
gtctcgtggg ctcggagatg tgtataagag acagnnnnac ctaaccaaaa ataacccaaa    60
aac                                                                 63

<210> SEQ ID NO 47
<211> LENGTH: 56
<212> TYPE: DNA
<213> ORGANISM: Artificial Sequence
<220> FEATURE:
<223> OTHER INFORMATION: MIR296-forward
<220> FEATURE:
<221> NAME/KEY: misc_feature
<222> LOCATION: (34)..(37)
<223> OTHER INFORMATION: n is a, c, g, or t

<400> SEQUENCE: 47
tcgtcggcag cgtcagatgt gtataagaga cagnnnnggg tattggggaa tggtga        56

<210> SEQ ID NO 48
<211> LENGTH: 58
<212> TYPE: DNA
<213> ORGANISM: Artificial Sequence
<220> FEATURE:
<223> OTHER INFORMATION: MIR296-reverse
<220> FEATURE:
<221> NAME/KEY: misc_feature
<222> LOCATION: (35)..(38)
<223> OTHER INFORMATION: n is a, c, g, or t

<400> SEQUENCE: 48
gtctcgtggg ctcggagatg tgtataagag acagnnnncr aaaaccccaa acctaaca     58

<210> SEQ ID NO 49
<211> LENGTH: 57
<212> TYPE: DNA
<213> ORGANISM: Artificial Sequence
<220> FEATURE:
<223> OTHER INFORMATION: LRRTM1-forward
<220> FEATURE:
<221> NAME/KEY: misc_feature
<222> LOCATION: (34)..(37)
<223> OTHER INFORMATION: n is a, c, g, or t

<400> SEQUENCE: 49
tcgtcggcag cgtcagatgt gtataagaga cagnnnngtt tggtggaggg aaggagt      57

<210> SEQ ID NO 50
<211> LENGTH: 58
<212> TYPE: DNA
<213> ORGANISM: Artificial Sequence
<220> FEATURE:
<223> OTHER INFORMATION: LRRTM1-reverse
<220> FEATURE:
<221> NAME/KEY: misc_feature
<222> LOCATION: (35)..(38)
<223> OTHER INFORMATION: n is a, c, g, or t

<400> SEQUENCE: 50
```

```
gtctcgtggg ctcggagatg tgtataagag acagnnnnta accracrcca ccttttac          58
```

<210> SEQ ID NO 51
<211> LENGTH: 63
<212> TYPE: DNA
<213> ORGANISM: Artificial Sequence
<220> FEATURE:
<223> OTHER INFORMATION: hTERT-forward
<220> FEATURE:
<221> NAME/KEY: misc_feature
<222> LOCATION: (34)..(37)
<223> OTHER INFORMATION: n is a, c, g, or t

<400> SEQUENCE: 51

```
tcgtcggcag cgtcagatgt gtataagaga cagnnnnggt ttttgtattt tattttttgtg    60
gtt                                                                    63
```

<210> SEQ ID NO 52
<211> LENGTH: 62
<212> TYPE: DNA
<213> ORGANISM: Artificial Sequence
<220> FEATURE:
<223> OTHER INFORMATION: hTERT-reverse
<220> FEATURE:
<221> NAME/KEY: misc_feature
<222> LOCATION: (35)..(38)
<223> OTHER INFORMATION: n is a, c, g, or t

<400> SEQUENCE: 52

```
gtctcgtggg ctcggagatg tgtataagag acagnnnncc aacttcctca aaccctattt     60
aa                                                                    62
```

<210> SEQ ID NO 53
<211> LENGTH: 162
<212> TYPE: DNA
<213> ORGANISM: Artificial Sequence
<220> FEATURE:
<223> OTHER INFORMATION: PARP15 amplicon

<400> SEQUENCE: 53

```
cgaccccccag agaacttatg cacggagttg caggtgttac ttccagagcc ggacgagatc    60
gggaggcggg gagcgtgctg ccggccggga accgtggggc gcggaaggcc tcccggcgct    120
cttcctcccg gagtatggtg aggagcgcgg gggacgggtg cg                       162
```

<210> SEQ ID NO 54
<211> LENGTH: 167
<212> TYPE: DNA
<213> ORGANISM: Artificial Sequence
<220> FEATURE:
<223> OTHER INFORMATION: ITGA4

<400> SEQUENCE: 54

```
tcacgtctga gcgcacgtgc acgtgtctcg ctttaggctc ctagtgggtg cgcccactgc    60
caactggctc gccaacgctt cagtgatcaa tcccggggcg atttacagat gcaggatcgg   120
aaagaatccc ggccagacgt gcgaacagct ccagctgggt gagttgg                  167
```

<210> SEQ ID NO 55
<211> LENGTH: 144
<212> TYPE: DNA
<213> ORGANISM: Artificial Sequence
<220> FEATURE:
<223> OTHER INFORMATION: NTM

<400> SEQUENCE: 55

```
gaagcggctc ctgagacgcg cccacacctt tcacctgccg cgcgcttccc cctcctcggc      60
caccttcccg gcggaagcag cgaggaggga gcccccttg gccgtcctcc gtggaaccgg     120
ttttccgagg ctggcaaaag ccga                                           144
```

<210> SEQ ID NO 56
<211> LENGTH: 136
<212> TYPE: DNA
<213> ORGANISM: Artificial Sequence
<220> FEATURE:
<223> OTHER INFORMATION: ZAP70

<400> SEQUENCE: 56

```
gcgagttcta ctcgcgcgac cccgacgggc tgccctgcaa cctgcgcaag ccgtgcaacc      60
ggccgtcggg cctcgagccg cagccggggg tcttcgactg cctgcgagac gccatggtgc     120
gtgactacgt gcgcca                                                    136
```

<210> SEQ ID NO 57
<211> LENGTH: 209
<212> TYPE: DNA
<213> ORGANISM: Artificial Sequence
<220> FEATURE:
<223> OTHER INFORMATION: MIR193A

<400> SEQUENCE: 57

```
ttggagcccg cgacccgagg tcgggcgggg cggtggactt tcccggggaa cgccgcctga      60
gggacaccca gagcttcggc ggagcggagc gcggtgcaca gagccggcga ccggacccag     120
ccccgggaag cccgtcgggg acgcaccccg aactccgagg atgggagctg agggctgggt     180
ctttgcgggc gagatgaggg tgtcggatc                                      209
```

<210> SEQ ID NO 58
<211> LENGTH: 224
<212> TYPE: DNA
<213> ORGANISM: Artificial Sequence
<220> FEATURE:
<223> OTHER INFORMATION: EPHX3

<400> SEQUENCE: 58

```
gccgccgtgg tcccggagcg cggcgacatg ccggagctgg tggtgaccgc gctgctggcg      60
ccgtcgcgcc tgtcgctgaa gctgctgcgc gccttcatgt ggagcctggt gttctcggtg     120
gcgctggtgg ccgcggcggt ctacggctgc atagcgctca cgcacgtgct gtgccggccc     180
cggcgcggct gctgcgggcg ccgtcggagc gcgtccccg cctg                      224
```

<210> SEQ ID NO 59
<211> LENGTH: 142
<212> TYPE: DNA
<213> ORGANISM: Artificial Sequence
<220> FEATURE:
<223> OTHER INFORMATION: KIF1A

<400> SEQUENCE: 59

```
tcggacgccg cgcgcagcca accagcgcct cgggagggc gcggggcggt ccgggccggg      60
ggcgcgcagc ccgtcacgcg gcggcgccgt cacagcgcag agcagccggc gagcggcagc     120
agctccgggc tcgagagccc gc                                             142
```

<210> SEQ ID NO 60
<211> LENGTH: 152

```
<212> TYPE: DNA
<213> ORGANISM: Artificial Sequence
<220> FEATURE:
<223> OTHER INFORMATION: LINC00599

<400> SEQUENCE: 60
accgtgggtc ggcgagggcc cgccaaggaa ggagcgaccg accgagccag gcgccctccg      60
cagacctccg cgcagcggcc gcgggcgcga ggggaggggt ctggagctcc ctccggctgc     120
ctgtcccgca ccggagcccg tggggtgggg ag                                    152

<210> SEQ ID NO 61
<211> LENGTH: 141
<212> TYPE: DNA
<213> ORGANISM: Artificial Sequence
<220> FEATURE:
<223> OTHER INFORMATION: FLI1

<400> SEQUENCE: 61
ctcgcagggg gcacgcaggg agggcccagg gcgccaggga ggccgcgccg ggctaatccg      60
aaggggctgc gaggtcaggc tgtaaccggg tcaatgtgtg gaatattggg gggctcggct     120
gcagacttgg ccaaatggac g                                                141

<210> SEQ ID NO 62
<211> LENGTH: 132
<212> TYPE: DNA
<213> ORGANISM: Artificial Sequence
<220> FEATURE:
<223> OTHER INFORMATION: GP1BB

<400> SEQUENCE: 62
tgttggtgaa cgtcgcagcg ggtgtccgag tgctccgtgt gccctgaga gcgggtggga      60 gcggaagcct gagcggcctg cggcctccgg cgatagtgtg ctatctgccg ctgcagcgcg    120
cgtccgcgcg gc                                                          132

<210> SEQ ID NO 63
<211> LENGTH: 191
<212> TYPE: DNA
<213> ORGANISM: Artificial Sequence
<220> FEATURE:
<223> OTHER INFORMATION: MIR296

<400> SEQUENCE: 63
gccgtgccgc gcctctgcca cagtctcccg tgggtcccca ctgccgggag ttttacctac      60
ctcccaccct cagccacgag cacctgcagg atgcggtgcc atcctcgccg gtgcccgctc    120
cccttccgga ggctctctcc accctcactg acgcctcctc gggaaagccc ccgctccttc    180
cccgacctca c                                                           191

<210> SEQ ID NO 64
<211> LENGTH: 132
<212> TYPE: DNA
<213> ORGANISM: Artificial Sequence
<220> FEATURE:
<223> OTHER INFORMATION: LRRTM1

<400> SEQUENCE: 64
ggcgccgctc gccgctcccc gcgccgccgt ccgcacctcc ccaccgcccg ccgcccgccg      60
cccgccgccc gcaaagcatg agtgagcccg ctctctgcag ctgcccgggg gcgcgaatggc    120 aggctgtttc cg                                                          132
```

<210> SEQ ID NO 65
<211> LENGTH: 109
<212> TYPE: DNA
<213> ORGANISM: Artificial Sequence
<220> FEATURE:
<223> OTHER INFORMATION: Human TERT

<400> SEQUENCE: 65
gctgcggtgg ctgcggtgac cccgtcatct gaggagagtg tggggtgagg tggacagagg    60
tgtggcatga ggatcccgtg tgcaacacac atgcggccag gaacccgtt              109

<210> SEQ ID NO 66
<211> LENGTH: 60
<212> TYPE: DNA
<213> ORGANISM: Artificial Sequence
<220> FEATURE:
<223> OTHER INFORMATION: IonTorrent A

<400> SEQUENCE: 66
ccatctcatc cctgcgtgtc tccgactcag ctaaggtaac gatgtaatac gacggtcagt    60

<210> SEQ ID NO 67
<211> LENGTH: 40
<212> TYPE: DNA
<213> ORGANISM: Artificial Sequence
<220> FEATURE:
<223> OTHER INFORMATION: IonTorrent P

<400> SEQUENCE: 67
cctctctatg ggcagtcggt gatcaggaaa cagctatgac                          40

<210> SEQ ID NO 68
<211> LENGTH: 70
<212> TYPE: DNA
<213> ORGANISM: Artificial Sequence
<220> FEATURE:
<223> OTHER INFORMATION: P5 index 503

<400> SEQUENCE: 68
aatgatacgg cgaccaccga gatctacact atcctcttcg tcggcagcgt cagatgtgta    60
taagagacag                                                           70

<210> SEQ ID NO 69
<211> LENGTH: 66
<212> TYPE: DNA
<213> ORGANISM: Artificial Sequence
<220> FEATURE:
<223> OTHER INFORMATION: P7 index 702

<400> SEQUENCE: 69
caagcagaag acggcatacg agatctagta cggtctcgtg gctcggaga tgtgtataag    60 agacag                                                               66

<210> SEQ ID NO 70
<211> LENGTH: 17
<212> TYPE: DNA
<213> ORGANISM: Artificial Sequence
<220> FEATURE:
<223> OTHER INFORMATION: Forward Universal A

<400> SEQUENCE: 70
gtaatacgac ggtcagt                                                   17

```
<210> SEQ ID NO 71
<211> LENGTH: 17
<212> TYPE: DNA
<213> ORGANISM: Artificial Sequence
<220> FEATURE:
<223> OTHER INFORMATION: reverse Universal B

<400> SEQUENCE: 71
caggaaacag ctatgac                                                    17

<210> SEQ ID NO 72
<211> LENGTH: 52
<212> TYPE: DNA
<213> ORGANISM: Artificial Sequence
<220> FEATURE:
<223> OTHER INFORMATION: ADPTUNIAFwMID2

<400> SEQUENCE: 72
cgtatcgcct ccctcgcgcc atcagacgct cgacagtaat acgacggtca gt             52

<210> SEQ ID NO 73
<211> LENGTH: 52
<212> TYPE: DNA
<213> ORGANISM: Artificial Sequence
<220> FEATURE:
<223> OTHER INFORMATION: ADPTUNIBRvMID5

<400> SEQUENCE: 73
ctatgcgcct tgccagcccg ctcagatcag acacgcagga aacagctatg ac             52

<210> SEQ ID NO 74
<211> LENGTH: 60
<212> TYPE: DNA
<213> ORGANISM: Artificial Sequence
<220> FEATURE:
<223> OTHER INFORMATION: Primer A IonXpress 1

<400> SEQUENCE: 74
ccatctcatc cctgcgtgtc tccgactcag ctaaggtaac gatgtaatac gacggtcagt     60

<210> SEQ ID NO 75
<211> LENGTH: 40
<212> TYPE: DNA
<213> ORGANISM: Artificial Sequence
<220> FEATURE:
<223> OTHER INFORMATION: Primer P

<400> SEQUENCE: 75
cctctctatg ggcagtcggt gatcaggaaa cagctatgac                           40
```

METHOD FOR DETERMINING A HEAD AND NECK SQUAMOUS CELL CARCINOMA

This application is a U.S. national stage of PCT/IB2017/056875 filed on 3 Nov. 2017 which claims priority to and the benefit of Italian patent application No. 102016000111174 filed on Nov. 4, 2016, the content of which are incorporated herein by reference in their entireties.

Sequence listing ASCII file Untitled ST25.txt, created on Apr. 6, 2020 and of size of 18,840 bytes is incorporated herein by reference.

DESCRIPTION

The present invention refers to a method performed in vitro to determine a Head and Neck Squamous Cell Carcinoma, preferably at early stage, based on the measuring of the hypermethylation and/or hypomethylation level(s) of CpGs/CpG islands of specific set of genes.

BACKGROUND

Oral and pharyngeal cancer, grouped together, are the sixth most common cancer in the world. The annual estimated incidence is approximately 600,000 per year, two-thirds of these cases occurring in developing countries. The mortality rates of these tumors have remained unchanged (50% within 5 years after diagnosis) and are mostly related to tobacco smoking and alcohol intake. Oral cancer patients are usually diagnosed in an advanced stage, which is associated with worse prognosis and higher radio- and chemo-therapy morbidity. Moreover, patient's quality of life is extremely compromised, since surgical therapy usually involves mutilating which often has significant effects on swallowing, speech, and physical appearance.

In particular, Oral Squamous Cell Carcinoma (OSCC) is the most frequent Head and Neck Squamous Cell Carcinoma (HNSCC—the neoplastic diseases affecting head and neck regions) and is usually preceded by oral pre-malignant lesions (OPML). Clinical and histological features of OPML are not able to provide enough information to identify the lesions, leading to a high risk of enduring malignant transformation and develop an OSCC during follow-up. In addition, patients affected by OSCC can developed a second primary OSCC, with a frequency ranging between 17% and 30%.

Although the oral cavity is easily accessible for examination, several factors limit the identification and early treatment of OPMLs. For this purpose, the current gold standard for screening and detecting, is the visual and tactile palpation during an extra- and intraoral examination by the healthcare professional in a routine dental or physical examination.

However, this disease is not easy to identify in its earliest stages and has often eluded medical and dental professionals because it can be "occult," or hidden from plain view. Indeed, normal-looking tissue may often hide the truth within the cells below the mucosa's surface.

If the disease is identified in earlier stages (Stage I or Stage II)—the ideal time for identification is before the dysplastic cells have been able to break through the basement membrane—the overall five-year survival rate is greater than 80 percent.

Unfortunately, all too often the manifestations of this invasive and devastating disease are detected in the late stages (Stages III-IV), when the lesions have typically advanced so deeply that it is impossible to treat without radical surgical intervention and significant loss of the patient's quality of life.

In particular, OSCC or High Grade Squamous Intraepithelial Lesion (HG-SIL) are usually diagnosed based on an incisional biopsy. Nevertheless, the incisional biopsy requires a minimally invasive surgical approach that can create discomfort and be refused by the patient.

It looks evident from the comments reported above that improved oral cancer prevention, early detection, diagnostic, and clinical management tools are needed to identify high-risk patients, such as those exposed to smoking and alcohol consumption, patients without adequate access to health care, and with high-risk lesions such as leukoplakia, which may progress to carcinoma lesions. In particular, considering how much HNPCC is widespread, there is a huge need of developing a non-invasive method to early detect this kind of tumors, and in particular oral premalignant lesions (OPML) which may develop neoplastic lesions, in order to reduce the burden of OSCC.

Over the last decade, Quantitative Methylation Specific PCR (qMSP) preceded by bisulfite treatment has been proposed as a method to evaluate biomarkers useful in OSCC detection. In this regard, various genes have been previously studied for promoter methylation status in OSCC tissues. Guerrero-Preston et al, 2014 and the related patent application WO2015066170A1 refer to a comprehensive integrated genomic and epigenomic analysis in HNSCC, focusing on identifying genes that have concurrent promoter methylation, mutation and expression downregulation. In particular, these documents evaluated the methylation pattern of PAX1, PAX5, ZIC4 and PLCB1.

Moreover, Morandi et al. developed a non-invasive method to early detect OSCC and HG-SIL by epigenetic modifications analysis in the oral mucosa evaluating GP1BB and ZAP70 methylation status (Morandi, L. 2015).

However, the above-mentioned study is limited for number of cases and for low sensitivity and specificity of the method. Therefore, is still felt the need to identify methods allowing early and accurate detection of HNSCC, in particular HG-SIL/OSCC. This is not easy to obtain also because identifying the key genes and locating the informative and efficient methylation sites on their sequences are not trivial and obvious activities. Indeed, it is well known, for example that the gene network involved in carcinogenesis is really complex and wide and that the promoter region of genes spans more than one thousand base pairs and contains approximately one hundred potential methylation sites.

The present invention solves the needs reported above with a method involving the measurement of the hypermethylation and/or hypomethylation level(s) of informative CpGs/CpG islands in specific genomic regions of a selected number of genes.

The ability to correlate the methylation levels of several CpGs/CpG islands of a selected number of genes grants the method an accuracy beyond any other methods currently available. Moreover, the disclosed method allows the early detection of HNSCC with high specificity and sensitivity starting from a biological sample, such as an oral brushing.

BRIEF DISCLOSURE OF THE DRAWINGS

FIG. 1A-B show the flow chart of an example of application of the method of the invention to a specific set of genes.

Figure 2C:
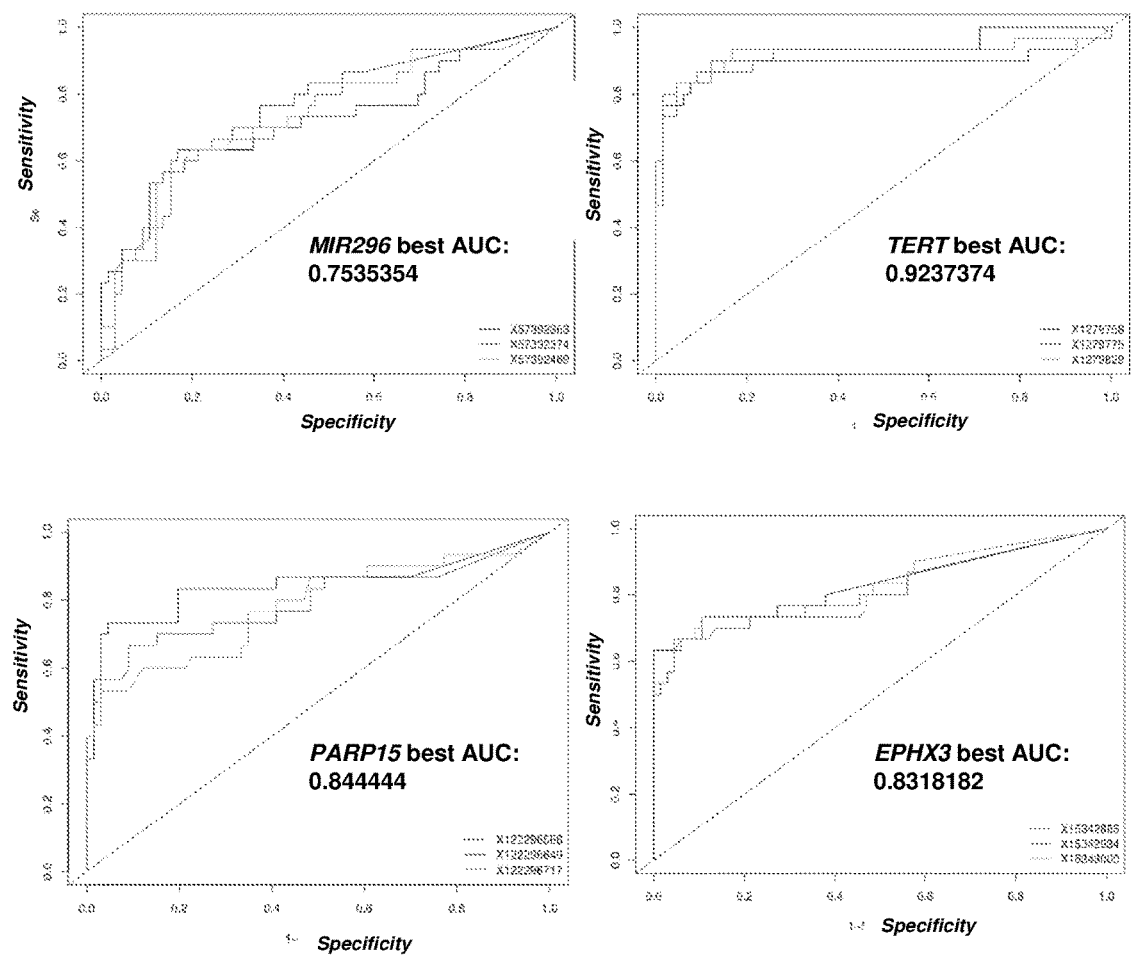

FIG. 2A-C show the ROC analysis discriminating OSCC vs normal healthy donors showing the three best performing CpGs from each gene.

FIG. 3A-D show the methylation profile plot from the genes evaluated. For each group of samples the lines represent the methylation mean for each position. Asterisks indicate a statistical significance as calculated by the Kruskal-Wallis test.

Figure 4:
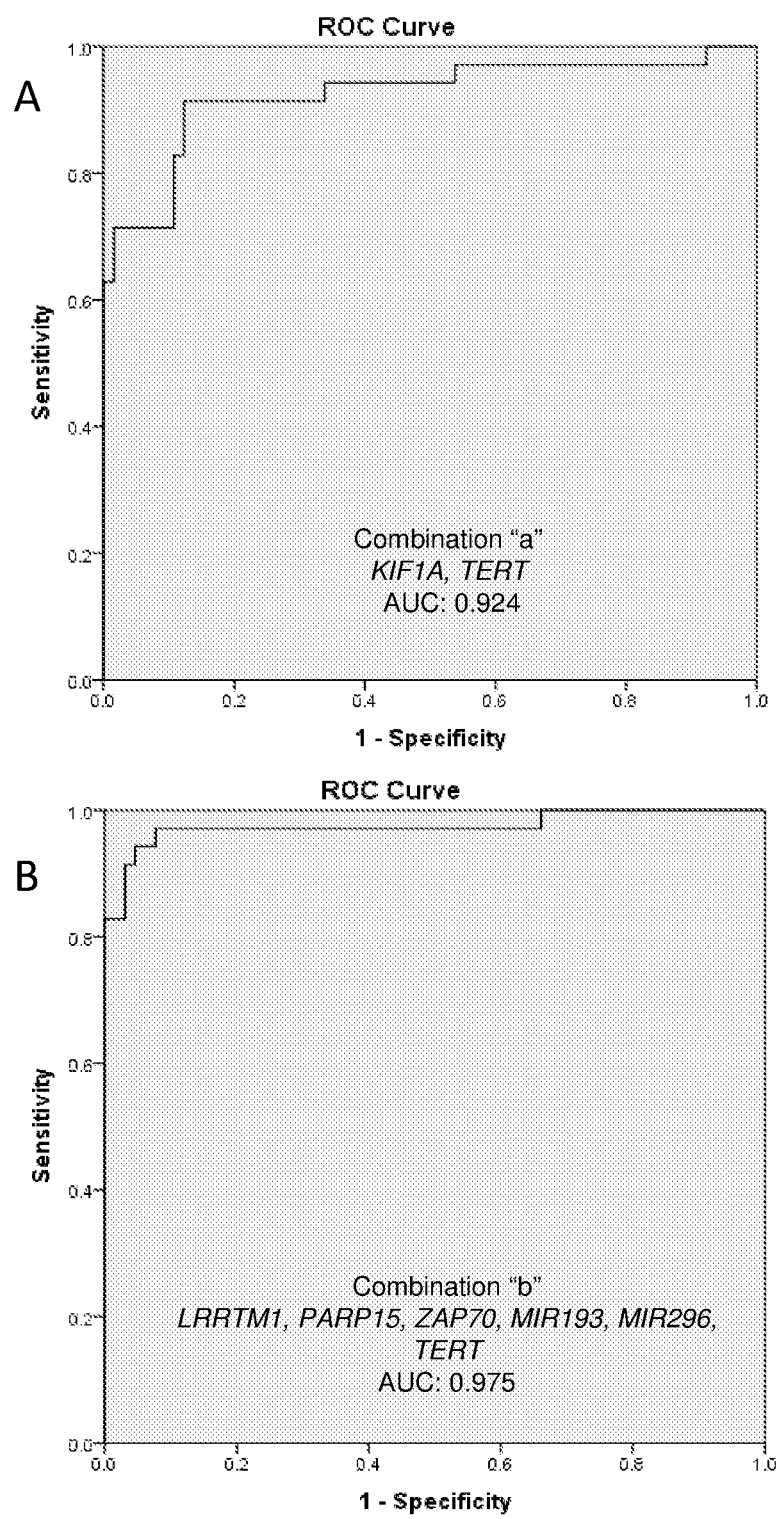
Figure 5:
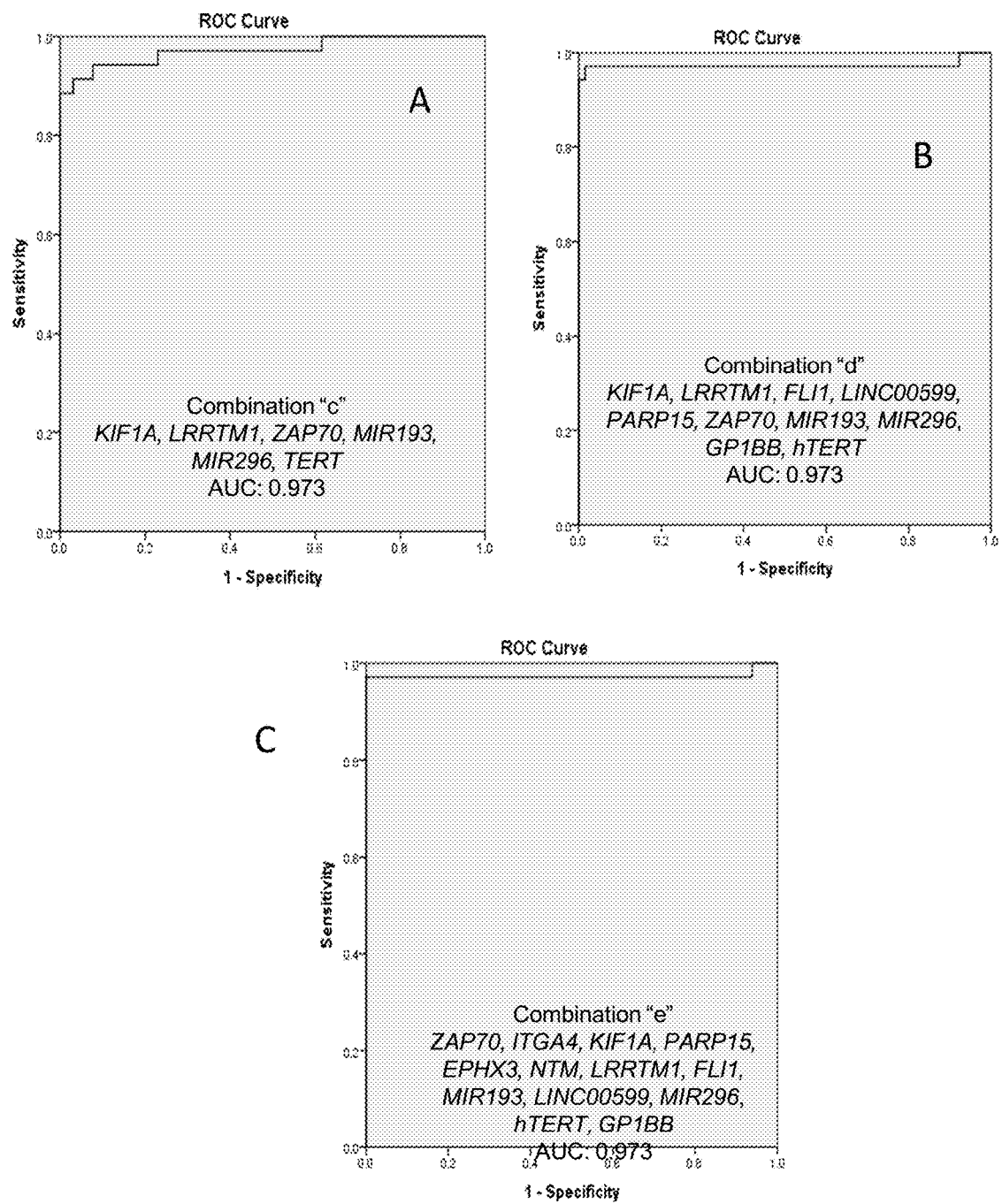

FIGS. 4 and 5 show the ROC analysis of the specific combinations of genes exemplified. FIG. 4A refer to KIF1A and TERT, FIG. 4B refers to LRRTM1, PARP15, ZAP70, MIR193, MIR 296 and TERT, FIG. 5A refers to KIF1A, LRRTM1, ZAP70, MIR193, MIR 296 and TERT, FIG. 5B refers to KIF1A, LRRTM1, LINC00599, PARP15, ZAP70, MIR193, MIR 296, GP1 BB and hTERT, and FIG. 5C refers to KIF1A, LRRTM1, ZAP70, MIR193, MIR 296, ITGA4, PARP15, EPHX3, FLI1, GP1 BB and hTERT.

Figure 6:
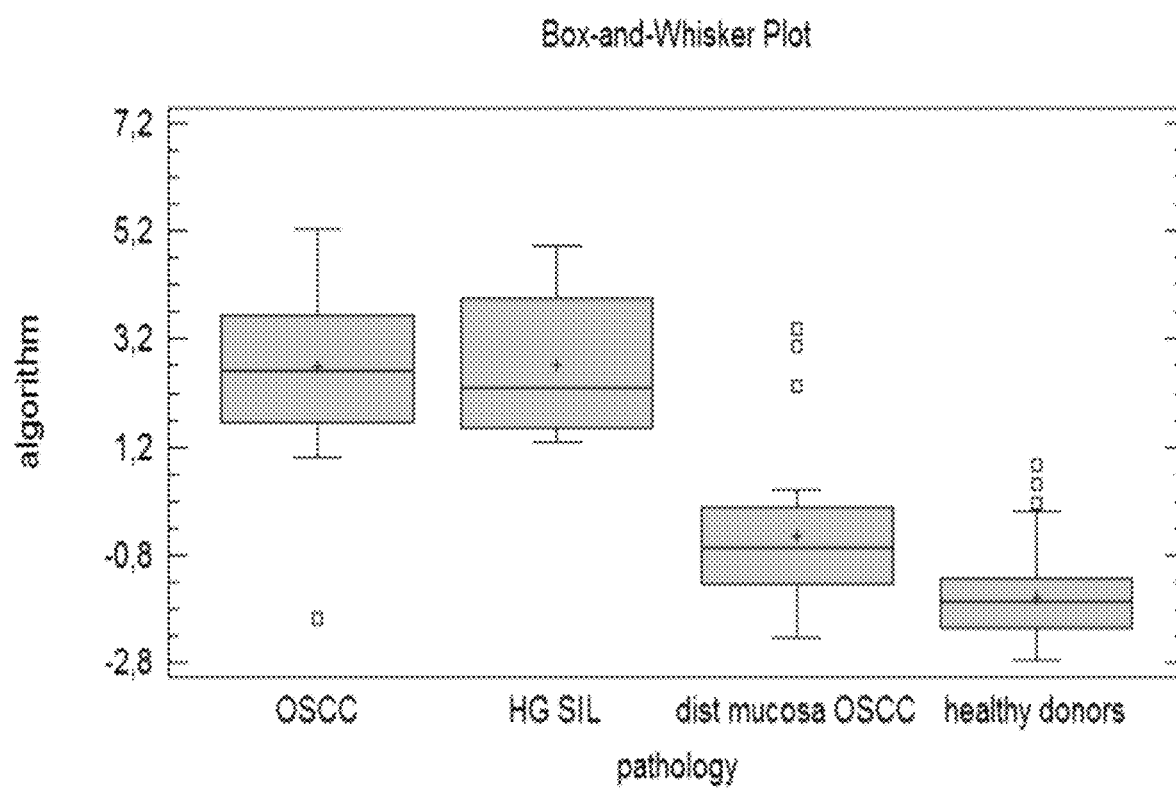

FIG. 6 shows the box plots obtained using the scores calculated from the algorithm showed a between-group significant difference (Kruskal-Wallis test T=78,8587, $p<0.05$).

DEFINITIONS

In the context of the present invention, "Head and Neck Squamous Cell Carcinoma (HNSCCs)" are tumors developing in the mucous membranes of mouth, nose, or throat and, generally, classified by their location. Indeed, this kind of carcinoma can occur in the mouth (oral cavity), in the middle part of the throat near the mouth (oropharynx), in the space behind the nose (nasal cavity and paranasal sinuses), in the upper part of the throat near the nasal cavity (nasopharynx), in the larynx, or in the lower part of the throat near the larynx (hypopharynx).

In the context of the present invention, "Oral Squamous Cell Carcinoma (OSCC)" represents 95% of all forms of HNSCC and during the past decade, its incidence has increased by 50%. OSCC, emerge from the accumulation of genetic changes and epigenetic anomalies in the signaling pathways that are associated with cancer, resulting in phenotypes that facilitate OSCC development. It derives from the stratified squamous epithelium of the oral mucosa. The majority of OSCC are diagnosed at a late phase, in stages Ill or IV, which markedly decreases the chances of survival and leads to a significant deterioration in patient quality of life.

"High Grade Squamous Intraepithelial Lesion (HG-SIL)" has been introduced by Gale et al. 2014. The classification provides two grades: 1) low-grade, and 2) high-grade lesions and, specifically for the larynx, an additional grade-carcinoma in situ (CIS) which must be separated from high-grade laryngeal SILs. This study provided clear morphological criteria with which to define prognostic groups. The retrospective follow-up study demonstrated a highly significant difference in the risk of malignant progression between low grade and high-grade lesions improving patient management and clinical decision-making.

In the context of the present invention, "Oral Pre-Malignant Lesion (OPML)" is a morphologically altered tissue in which oral cancer is more likely to occur than in its apparently normal counterpart. Recently, the World Health Organization (WHO) identified the following OPML: leukoplakia, erythroplakia, palatal lesion of reverse cigar smoking, oral lichen planus, oral submucous fibrosis (SMF) and discoid lupus erythematosus.

In the context of the present invention, "DNA methylation" means epigenetic modifications of nucleic acids that alter their accessibility and structure, preferably chromatin structure, thereby regulating patterns of gene expression. They can be modified by exogenous influences and, as such, can contribute to or be the result of environmental alterations of phenotype or pathophenotype.

In the context of the present invention, "CpG islands" are regions of the human genome with elevated G+C content. These regions have generally about 1 kb length and, usually overlap the promoter region of 60-70% of all human genes. They are also present in repeats as transposable elements and functions to repress transcription. Within these regions, the majority of CpG pairs are chemically modified by the covalent attachment of a methyl group to the C5 position of the cytosine ring. Aberrant DNA methylation of CpGs in the proximity of transcription start sites often leads to alterations in gene function and pathway deregulation in human cancer.

In the context of the present invention, "genomic DNA region" means regions of nucleic acid, preferably DNA, more preferably genomic DNA such as the gene promoter, the 5'UTR, the gene body, the 3'UTR and shores (refers to DNA sequence that occur up to about 2 kb distant from a CpG island of comparatively low CpG density that are located near traditional CpG islands).

DETAILED DESCRIPTION

A first aspect of the present invention refers to a method for detecting (for determining the presence of) a Head and Neck Squamous Cell Carcinoma (HNSCC) comprising the steps of:
(i) Obtaining an isolated biological sample from an individual;
(ii) Purifying a nucleic acid, preferably the DNA, more preferably the genomic DNA, from said sample;
(iii) Treating the purified nucleic acid, preferably the DNA, with bisulfite, preferably sodium bisulfite;
(iv) Amplifying the nucleic acid after step (iii) by using at least one primer pair said primer pair allowing the amplification of at least one sequence of the genomic region of at least one gene (in other words at least one portion of the genomic/chromosomic region of a gene, that is a portion of its genomic mapping site comprising the coding and regulative regions of the gene) wherein 1) said gene is selected from: EPHX3, KIF1A, LRRTM1, FLI1, ITGA4, LINC00599, NTM, PARP15, ZAP70, miR193, miR296, GP1BB, hTERT and any combination thereof, and 2) said sequence comprises at least one CpG, preferably at least one CpG island;
(v) Measuring the methylation level of the at least one CpG/CpG island of the amplified sequence of the genomic region of at least one of the following genes EPHX3, KIF1A, LRRTM1, FLI1, ITGA4, LINC00599, NTM, PARP15, ZAP70, miR193, miR296, GP1BB, hTERT or any combination thereof, preferably at least one of the following set of genes:
a) Human TERT and KIF1A; and/or
b) LRRTM1, PARP15, ZAP70, miR193, miR296, hTERT; and/or
c) KIF1A, LRRTM1, ZAP70, miR193, miR296, hTERT; and/or
d) KIF1A, LRRTM1, FLI1, LINC00599, PARP15, ZAP70, miR193, miR296, GP1BB, hTERT; and/or
e) EPHX3, KIF1A, LRRTM1, FLI1, ITGA4, LINC00599, NTM, PARP15, ZAP70, miR193, miR296, GP1BB, hTERT,
wherein the hypermethylation of the at least one CpG/CpG island falling in the sequence of at least one of the following genes of the sets: EPHX3, KIF1A, LRRTM1, FLI1, ITGA4, LINC00599, NTM, PARP15, ZAP70, miR193 and/or the hypomethylation of the at least one CpG/CpG island falling in the sequence of at least one of the following genes of the sets: miR296, GP1BB, hTERT is(are) indicative of a HNSCC positive sample wherein the hypermethylation and/or hypomethylation is/are evaluated with respect to the methylation level measured for the same CpGs/CpG islands of the same regions of the same genes in a sample isolated from a healthy individual (negative control), preferably in a population of healthy individuals.

FIGS. 1-A and B summarize in a flow chart the key steps of the method of the invention. In particular, the flow chart refers to a non-limiting example of an application of the method of the invention to a specific set of genes.

FIG. 1-A summarizes a specific embodiment of the invention involving 1) collecting the biological sample and purifying the DNA; 2) treating the DNA with bisulfite; and 3) amplifying the genomic regions of interest.

FIG. 2-B summarizes a specific embodiment exemplifying the methylation level measurement step, in other words the last phase of the method allowing the determination of the eventual positivity of the sample for a HNSCC.

The method of the invention allows determining if the biological sample belongs to an individual affected by a HNSCC (HNSCC positive). Preferably, the HNSCC is detected (determined) at early stage. Therefore, the detection is an early stage detection. Thus, the method can be also used as prognostic tool and/or for the follow up of a therapeutic treatment of a HNSCC. Finally, the method of the invention is also useful in the prevention of these kind of carcinomas.

Therefore, the method of the invention is also for prognosing a Head and Neck Squamous Cell Carcinoma and/or for the follow up of a therapeutic treatment of a HNSCC and/or for the prevention of a HNSCC.

In this context, EPHX3 is acronym of epoxide hydrolase or the following synonyms: FLJ22408, ABHD9, EH3; KIF1A is acronym of kinesin family member 1 or the following synonyms: UNC104, C2orf20, ATSV, HSN2C, SPG30, MRD9; LRRTM1 is acronym of leucine rich repeat transmembrane neuronal 1 or the following synonyms: FLJ32082; FLI1 is acronym of Fli-1 proto-oncogene, ETS transcription factor or the following synonyms: EWSR2, SIC-1; ITGA4 is acronym of integrin subunit alpha 4 or the following synonyms: IA4, CD49D; LINC00599 is acronym of long intergenic non-protein coding RNA 599 or the following synonyms: MIRN124A1, MIRN124-1, MIR124A1, MIR124A, Rncr3, mir-124-1; NTM is acronym of neurotrimin or the following synonyms: NT, NTRI, IGLON2, HNT; PARP15 is acronym of poly(ADP-ribose) polymerase family member 15 or the following synonyms: FLJ40597, pART7, ARTD7, BAL3; ZAP70 is acronym of zeta chain of T cell receptor associated protein kinase 70 or the following synonyms: IMD48, TZK, STD, ZAP-70, SRK, STCD, ADMIO2; miR193 is acronym of microRNA 193a or the following synonyms: MIRN193A, mir-193a, hsa-mir-193a, hsa-mir-193, MIRN193; miR296 is acronym of microRNA 296 or the following synonyms: hsa-mir-296, mir-296, MIRN296, miRNA296; GP1BB is acronym of glycoprotein 1b platelet beta subunit or the following synonyms: GPIBB, GPIbbeta, CD42C, BS, BDPLT1, CD42c; hTERT is acronym of telomerase reverse transcriptase or the following synonyms: TRT, TCS1, DKCA2, EST2, PFBMFT1, CMM9, hEST2, DKCB4, hTRT, TP2.

In the context of the present invention, hypermethylation means that the measured methylation level of the at least one CpG/CpG island is increase in a tested sample (isolated from an individual suspected to be affected by a HNSCC) compared to a negative sample (a biological sample isolated from a healthy individual not affected by a HNSCC), wherein the negative sample is preferably a sample of DNA isolated from normal mucosa of healthy individuals not affected by a HNSCC.

In the context of the present invention, hypomethylation means that the measured methylation level of the at least one CpG/CpG island is reduced in a tested sample (isolated from an individual suspected to be affected by a HNSCC) compared to a negative sample (a biological sample isolated from a healthy individual not affected by a HNSCC), wherein the negative sample is preferably a sample of DNA isolated from normal mucosa of healthy individuals not affected by a HNSCC.

The biological sample of step (i) is isolated from an individual who can be affected or suspected to be affected by a HNSCC, preferably he has been surgically treated for a HNSCC, preferably a OSCC. According to a preferred embodiment, said HNSCC is any tumor developing in oral cavity, nose, and throat. Preferably, said HNSCC is any Oral Squamous Cell Carcinoma or its precursor, preferably High-Grade Squamous Intraepithelial Lesion (HG-SIL), or an Oral Premalignant Lesion or a cancerization field. Cancerization field means an area of mucosal epithelium made up of genetically altered cells eventually clonally related to the carcinoma, and therefore possible cause of local recurrence or secondary tumors.

According to a preferred embodiment, said Oral Premalignant Lesion (OPML) is preferably selected from: leukoplakia, erythroplakia, palatal lesion of reverse cigar smoking, oral lichen planus, oral submucous fibrosis (SMF), and discoid lupus erythematosus wherein an oral cancer is more likely to occur than in its apparently normal counterpart and can be detected by the present invention if the lesion is a real precursor of HNSCC.

Therefore, the method is ex vivo. The biological sample is any biological sample, preferably said sample is selected from: brushing from oral mucosa, plasma, saliva and any sample containing epithelial cells, preferably said cells being from oral cavity.

According to a preferred embodiment, the sample is isolated from the buccal cavity, preferably oral mucosa, more preferably by brushing, preferably by using a cytobrush or DNA buccal swab. This procedure allows obtaining a sample comprising exfoliated cells from buccal cavity, preferably from oral mucosa.

According to a preferred embodiment, the sample collection is preceded by oral rinses, at least 1-3 times, preferably with chlorhexidine 0.12% or any germicidal mouthwash. According to a further preferred embodiment, the sample collection is made by gently brushing a surface of the body region of interest, preferably said region showing a clinical lesion, preferably 1-10 times, more preferably about five times. It is advisable in the collecting procedure avoiding 1) to collect blood, and 2) to do not use any local anaesthetic.

The collected sample is preferably placed in a container containing a preservative solution (i.e. DNA/RNA Shield™), to allow nucleic acid preservation. More preferably, the sample is stored at low temperature, preferably about +4° C.

According to a further preferred embodiment, the sample undergoes to step (ii) involving isolating (extracting-purifying) a nucleic acid from the biological sample. Preferably, the nucleic acid isolated is DNA, preferably the genomic DNA. Any technique used in a laboratory to extract nucleic acids, in particular to extract high pure DNA, can be used, for example the MasterPure™ DNA purification kit.

After purification, the nucleic acid, preferably the purified genomic DNA, is treated with bisulfite, preferably sodium bisulfite (step iii).

Bisulfite converts an unmethylated cytosine (C) to uracil (U), such that uracil (U) is read thymine (T) when the treated nucleic acid is sequenced. This conversion does not affect a methylated C, which remains C in the sequence. Any method allowing to address this purpose should be considered an alternative to the bisulfite treatment and, therefore, part of the disclosure.

The bisulfite treatment of the nucleic acid is performed according to any common lab protocols or using commercially available kits, such as EZ Methylation-Lightning™ kit. Preferably, the bisulfite treatment is performed using an amount of nucleic acid, preferably of DNA, ranging from 50 ng to 10 g, preferably from 250 ng to 1 g.

Preferably, the bisulfite treatment involves a first step of denaturation of the nucleic acid, preferably at 98° C. for 10-20 minutes, more preferably about 8 minutes and/or the incubation of the denaturated nucleic acid with sodium bisulfite. Preferably, the bisulfite is used in a concentration of about 2.3-3.6 M, more preferably in the presence of hydroquinone, preferably in a concentration of about 10 mM. The reaction is preferably performed at a temperature ranging preferably from 45 to 60° C., more preferably from 50 to 55° C., still more preferably of about 54° C. for at least one hour.

At the end of the treatment, the nucleic acid is purified preferably by using a column technology and more preferably with a first ethanol based wash, a desulfonation step of 20 minutes at room temperature, two washing steps with buffered ethanol, and the elution step following the instruction of the provider.

After bisulfite treatment, the nucleic acid, preferably the DNA is amplified, preferably by using a PCR (polymerase Chain Reaction) protocol. The amplification is performed preferably by using at least one primer pair said primer pair allowing the amplification of at least one sequence, preferably a portion/sequence of the genomic region of at least one gene of interest said sequence comprising at least one CpG/CpG island. Preferably, the primer pair allows the amplification of a sequence of the genomic DNA region of at least one gene selected from: EPHX3, KIF1A, LRRTM1, FLI1, ITGA4, LINC00599, NTM, PARP15, ZAP70, miR193, miR296, GP1BB, hTERT and any combination thereof.

Preferably, at least one of the following combination of genes are amplified, meaning that at least one sequence of the genomic (DNA) region of at least one of the following combination of genes said region comprising at least one CpG/CpG island, is amplified in the method of the invention:
 a) Human TERT and KIF1A; and/or
 b) LRRTM1, PARP15, ZAP70, miR193, miR296, hTERT; and/or
 c) KIF1A, LRRTM1, ZAP70, miR193, miR296, hTERT; and/or
 d) KIF1A, LRRTM1, FLI1, LINC00599, PARP15, ZAP70, miR193, miR296, GP1BB, hTERT; and/or
 e) EPHX3, KIF1A, LRRTM1, FLI1, ITGA4, LINC00599, NTM, PARP15, ZAP70, miR193, miR296, GP1BB, hTERT.

However, any further combination of genes can be amplified according to the method of the invention.

Preferably, the genomic region of a gene means any regulating region of the gene, more preferably the promoter (generally upstream the ATG start site of a gene) region of the gene, the 5' and/or 3' UTRs, and/or any coding region (gene body), preferably exons and/or introns and/or shores.

According to a preferred embodiment of the invention, said region is preferably selected from SEQ ID NO: 53-65 wherein:
 SEQ ID NO: 53 is the region of PARP15 promoter spanning from 122296564 to 122296725 of the chromosome 3 strand+ with respect to hg19 coordinates showing the following CpGs/CpG islands having coordinates: 122296564, 122296586, 122296613, 122296617, 122296623, 122296630, 122296637, 122296645, 122296649, 122296656, 122296663, 122296671, 122296677, 122296680, 122296692, 122296708, 122296710, 122296717, 122296723;
 SEQ ID NO: 54 is the region of ITGA4 promoter spanning from 182322887 to 182323053 of the chromosome 2 strand+ with respect to hg19 coordinates showing the following CpGs/CpG islands having coordinates: 182322890, 182322898, 182322902, 182322908, 182322915, 182322937, 182322956, 182322962, 182322980, 182322985, 182323004, 182323016, 182323024, 182323028;
 SEQ ID NO: 55 is the region of NTM promoter spanning from 131781042 to 131781185 of the chromosome 11 strand+ with respect to hg19 coordinates showing the following CpGs/CpG islands having coordinates: 131781046, 131781058, 131781060, 131781080, 131781082, 131781084, 131781098, 131781110, 131781113, 131781122, 131781144, 131781151, 131781158, 131781167, 131781183;
 SEQ ID NO: 56 is the region of ZAP70 promoter spanning from 98340750 to 98340885 of the chromosome 12 strand+ with respect to hg19 coordinates showing the following CpGs/CpG islands having coordinates: 98340751, 98340762, 98340764, 98340766, 98340772, 98340775, 98340794, 98340801, 98340809, 98340813, 98340816, 98340823, 98340828, 98340834, 98340844, 98340854, 98340859, 98340869, 98340877, 98340881;
 SEQ ID NO: 57 is the region of MIR193A promoter spanning from 29886860 to 29887068 of the chromosome 17 strand+ with respect to hg19 coordinates showing the following CpGs/CpG islands having coordinates: 29886868, 29886870, 29886875, 29886881, 29886885, 29886890, 29886903, 29886910, 29886913, 29886936, 29886939, 29886944, 29886949, 29886951, 29886964, 29886967, 29886971, 29886983, 29886992, 29886995, 29887001, 29887008, 29887015, 29887045, 29887049, 29887063;
 SEQ ID NO: 58 is the region of EPHX3 promoter spanning from 15342826 to 15343049 of the chromosome 19 strand− with respect to hg19 coordinates showing the following CpGs/CpG islands having coordinates: 15342895, 15342889, 15342885, 15342875, 15342869, 15342866, 15342864, 15342855, 15342851, 15342848, 15342845, 15342840, 15342838, 15342831, 15343002, 15343000, 15342991, 15342988, 15342985, 15342983, 15342976, 15342962, 15342960, 15342934, 15342928, 15342918, 15342916, 15342913, 15342906; SEQ ID NO: 59 is the region of KIF1A promoter spanning from 241759586 to 241759727 of the chromosome 2 strand− with respect to hg19 coordinates showing the following CpGs/CpG islands having coordinates: 241759726, 241759722, 241759719, 241759717, 241759715, 241759702, 241759697, 241759688, 241759686, 241759681, 241759676, 241759671, 241759665, 241759663, 241759656, 241759651, 241759649, 241759646, 241759643, 241759640, 241759632, 241759621, 241759618, 241759614, 241759602, 241759596, 241759588;

SEQ ID NO: 60 is the region of LINC00599 promoter spanning from 9760739 to 9760890 of the chromosome 8 strand– with respect to hg19 coordinates showing the following CpGs/CpG islands having coordinates: 9760888, 9760881, 9760878, 9760870, 9760856, 9760852, 9760848, 9760839, 9760832, 9760822, 9760820, 9760815, 9760811, 9760809, 9760805, 9760803, 9760777, 9760764, 9760759, 9760752;

SEQ ID NO: 61 is the region of FLI1 promoter spanning from 128564020 to 128564160 of the chromosome 11 strand+ with respect to hg19 coordinates showing the following CpGs/CpG islands having coordinates: 128564022, 128564033, 128564051, 128564063, 128564065, 128564068, 128564078, 128564089, 128564106, 128564134, 128564158;

SEQ ID NO: 62 is the region of GP1BB promoter spanning from 19710829 to 19710960 of the chromosome 22 strand+ with respect to hg19 coordinates showing the following CpGs/CpG islands having coordinates: 19710839, 19710842, 19710847, 19710855, 19710864, 19710880, 19710890, 19710902, 19710909, 19710916, 19710919, 19710937, 19710944, 19710946, 19710948, 19710952, 19710954, 19710956;

SEQ ID NO: 63 is the region of MIR296 promoter spanning from 57392355 to 57392545 of the chromosome 20 strand– with respect to hg19 coordinates showing the following CpGs/CpG islands having coordinates: 57392543, 57392538, 57392536, 57392517, 57392501, 57392469, 57392452, 57392440, 57392437, 57392430, 57392419, 57392394, 57392386, 57392374, 57392363;

SEQ ID NO: 64 is the region of LRRTM1 promoter spanning from 80531676 to 80531807 of the chromosome 2 strand– with respect to hg19 coordinates showing the following CpGs/CpG islands having coordinates: 80531806, 80531803, 80531799, 80531796, 80531789, 80531786, 80531783, 80531780, 80531776, 80531763, 80531759, 80531756, 80531752, 80531749, 80531745, 80531742, 80531738, 80531719, 80531702, 80531697, 80531695, 80531677;

SEQ ID NO: 65 is the region of human TERT (hTERT) promoter spanning from 1279743 to 1279851 of the chromosome 21 strand– with respect to hg19 coordinates showing the following CpGs/CpG islands having coordinates: 1279847, 1279838, 1279829, 1279775, 1279758, 1279746.

In the context of the present invention, a locus of a CpG/CpG island has been mapped according to the human reference genome 19 (hg19), using blat, in which there is indication of chromosome number, position, positive or negative strand and percentage of identity.

According to a preferred embodiment, the at least one sequence of PARP15 amplified for the methylation level analysis according to step (iii) (amplicon is the name of the amplification product) is SEQ ID NO: 53 corresponding to the region of genomic DNA (strand+) mapped on chromosome 3 and having coordinates from 122296564 to 122296723 with respect to hg19 coordinates and the at least one CpG/CpG island evaluated on this sequence corresponds to a coordinate selected from: 122296564, 122296586, 122296613, 122296617, 122296623, 122296630, 122296637, 122296645, 122296649, 122296656, 122296663, 122296671, 122296677, 122296680, 122296692, 122296708, 122296710, 122296717, 122296723 and combination thereof, preferably is 122296586.

According to a preferred embodiment, the at least one sequence of ITGA4 amplified for the methylation level analysis according to step (iii) (amplicon) is SEQ ID NO: 54 corresponding to the region of genomic DNA (strand+) mapped on chromosome 2 and having coordinates from 182322887 to 182323053 with respect to hg19 coordinates and the at least one CpG/CpG island evaluated on this sequence corresponds to a coordinate selected from: 182322890, 182322898, 182322902, 182322908, 182322915, 182322937, 182322956, 182322962, 182322980, 182322985, 182323004, 182323016, 182323024, 182323028; and combination thereof, preferably is 182322902.

According to a preferred embodiment, the at least one sequence of NTM amplified for the methylation level analysis according to step (iii) (amplicon) is SEQ ID NO: 55 corresponding to the region of genomic DNA (strand+) mapped on chromosome 11 and having coordinates from 131781042 to 131781185 with respect to hg19 coordinates and the at least one CpG/CpG island evaluated on this sequence corresponds to a coordinate selected from: 131781046, 131781058, 131781060, 131781080, 131781082, 131781084, 131781098, 131781110, 131781113, 131781122, 131781144, 131781151, 131781158, 131781167, 131781183; and combination thereof, preferably is 131781082 or 131781167.

According to a preferred embodiment, the at least one sequence of ZAP70 amplified for the methylation level analysis according to step (iii) (amplicon) is SEQ ID NO: 56 corresponding to the region of genomic DNA (strand+) mapped on chromosome 12 and having coordinates from 98340750 to 98340885 with respect to hg19 coordinates and the at least one CpG/CpG island evaluated on this sequence corresponds to a coordinate selected from: 98340751, 98340762, 98340764, 98340766, 98340772, 98340775, 98340794, 98340801, 98340809, 98340813, 98340816, 98340823, 98340828, 98340834, 98340844, 98340854, 98340859, 98340869, 98340877, 98340881 and combination thereof, preferably is 98340751 or 98340854.

According to a preferred embodiment, the at least one sequence of MIR193 amplified for the methylation level analysis according to step (iii) (amplicon) is SEQ ID NO: 57 corresponding to the region of genomic DNA (strand+) mapped on chromosome 17 and having coordinates from 29886860 to 29887068 with respect to hg19 coordinates and the at least one CpG/CpG island evaluated on this sequence corresponds to a coordinate selected from: 29886868, 29886870, 29886875, 29886881, 29886885, 29886890, 29886903, 29886910, 29886913, 29886936, 29886939, 29886944, 29886949, 29886951, 29886964, 29886967, 29886971, 29886983, 29886992, 29886995, 29887001, 29887008, 29887015, 29887045, 29887049, 29887063 and combination thereof, preferably is 29886870 or 29886944.

According to a preferred embodiment, the at least one sequence of EPHX3 amplified for the methylation level analysis according to step (iii) (amplicon) is SEQ ID NO: 58 corresponding to the region of genomic DNA (strand –) mapped on chromosome 19 and having coordinates from 15342826 to 15343049 with respect to hg19 coordinates and the at least one CpG/CpG island evaluated on this sequence corresponds to a coordinate selected from: 15342895, 15342889, 15342885, 15342875, 15342869, 15342866, 15342864, 15342855, 15342851, 15342848, 15342845, 15342840, 15342838, 15342831, 15343002, 15343000, 15342991, 15342988, 15342985, 15342983, 15342976, 15342962, 15342960, 15342934, 15342928, 15342918, 15342916, 15342913, 15342906 and combination thereof, preferably is 15342840 or 15342885.

According to a preferred embodiment, the at least one sequence of KIF1A amplified for the methylation level analysis according to step (iii) (amplicon) is SEQ ID NO: 59 corresponding to the region of genomic DNA (strand −) mapped on chromosome 2 and having coordinates from 241759586 to 241759727 with respect to hg19 coordinates and the at least one CpG/CpG island evaluated on this sequence corresponds to a coordinate selected from: 241759726, 241759722, 241759719, 241759717, 241759715, 241759702, 241759697, 241759688, 241759686, 241759681, 241759676, 241759671, 241759665, 241759663, 241759656, 241759651, 241759649, 241759646, 241759643, 241759640, 241759632, 241759621, 241759618, 241759614, 241759602, 241759596, 241759588 and combination thereof, preferably is selected from: 241759686, 241759681, 241759651, and 241759621 and combination thereof;

According to a preferred embodiment, the at least one sequence of LINC00599 amplified for the methylation level analysis according to step (iii) (amplicon) is SEQ ID NO: 60 corresponding to the region of genomic DNA (strand −) mapped on chromosome 8 and having coordinates from 9760739 to 9760890 with respect to hg19 coordinates and the at least one CpG/CpG island evaluated on this sequence corresponds to a coordinate selected from: 9760888, 9760881, 9760878, 9760870, 9760856, 9760852, 9760848, 9760839, 9760832, 9760822, 9760820, 9760815, 9760811, 9760809, 9760805, 9760803, 9760777, 9760764, 9760759, 9760752 and combination thereof, preferably is 9760888.

According to a preferred embodiment, the at least one sequence of FLI1 amplified for the methylation level analysis according to step (iii) (amplicon) is SEQ ID NO: 61 corresponding to the region of genomic DNA (strand+) mapped on chromosome 11 and having coordinates from 128564020 to 128564160 with respect to hg19 coordinates and the at least one CpG/CpG island evaluated on this sequence corresponds to a coordinate selected from: 128564022, 128564033, 128564051, 128564063, 128564065, 128564068, 128564078, 128564089, 128564106, 128564134, 128564158 and combination thereof, preferably is 128564051 or 128564158.

According to a preferred embodiment, the at least one sequence of GP1BB amplified for the methylation level analysis according to step (iii) (amplicon) is SEQ ID NO: 62 corresponding to the region of genomic DNA (strand+) mapped on chromosome 22 and having coordinates from 19710829 to 19710960 with respect to hg19 coordinates and the at least one CpG/CpG island evaluated on this sequence corresponds to a coordinate selected from: 19710839, 19710842, 19710847, 19710855, 19710864, 19710880, 19710890, 19710902, 19710909, 19710916, 19710919, 19710937, 19710944, 19710946, 19710948, 19710952, 19710954, 19710956, and combination thereof, preferably is 19710946 or 19710956.

According to a preferred embodiment, the at least one sequence of MIR296 amplified for the methylation level analysis according to step (iii) (amplicon) is SEQ ID NO: 63 corresponding to the region of genomic DNA (strand −) mapped on chromosome 20 and having coordinates from 57392355 to 57392545 with respect to hg19 coordinates and the at least one CpG/CpG island evaluated on this sequence corresponds to a coordinate selected from: 57392543, 57392538, 57392536, 57392517, 57392501, 57392469, 57392452, 57392440, 57392437, 57392430, 57392419, 57392394, 57392386, 57392374, 57392363, and combination thereof, preferably is 57392363 or 57392374.

According to a preferred embodiment, the at least one sequence of LRRTM1 amplified for the methylation level analysis according to step (iii) (amplicon) is SEQ ID NO: 64 corresponding to the region of genomic DNA (strand −) mapped on chromosome 2 and having coordinates from 80531676 to 80531807 with respect to hg19 coordinates and the at least one CpG/CpG island evaluated on this sequence corresponds to a coordinate selected from: 80531806, 80531803, 80531799, 80531796, 80531789, 80531786, 80531783, 80531780, 80531776, 80531763, 80531759, 80531756, 80531752, 80531749, 80531745, 80531742, 80531738, 80531719, 80531702, 80531697, 80531695, 80531677 and combination thereof, preferably is 80531697 or 80531799.

According to a preferred embodiment, the at least one sequence of Human TERT (hTERT) amplified for the methylation level analysis according to step (iii) (amplicon) is SEQ ID NO: 65 corresponding to the region of genomic DNA (strand −) mapped on chromosome 21 and having coordinates from 1279743 to 1279851 with respect to hg19 coordinates and the at least one CpG/CpG island evaluated on this sequence corresponds to a coordinate selected from: 1279847, 1279838, 1279829, 1279775, 1279758, 1279746 and combination thereof, preferably is 1279775, 1279747 or 1279758.

According to a further preferred embodiment, phase (iii) of measuring the epigenetic modifications (methylation) of set (1)—KIF1A and human TERT—involves measuring 1) the hypermethylation of at least one of the CpG/CpG island of SEQ ID NO: 59 reported above, more preferably the CpG/CpG island having the coordinate 241759686, 241759681, 241759651, 241759621 of SEQ ID NO: 59 and/or 2) the hypomethylation of at least one of the CpG/CpG island of SEQ ID NO: 65 reported above, more preferably the CpG/CpG island having the coordinate 1279775 and/or, 1279747 and/or 1279758 of SEQ ID NO: 65.

According to a preferred embodiment phase (iii) of measuring the epigenetic modifications of set (2)—LRRTM1, PARP15, ZAP70, miR193, miR296, hTERT—involves measuring 1) the hypermethylation of at least one of the CpG/CpG island of SEQ ID NO: 64 for LRRTM1, SEQ ID NO: 53 for PARP15, SEQ ID NO: 56 for ZAP70, SEQ ID NO: 57 for miR193, more preferably the hypermethylation of the CpG/CpG island having the following coordinates: 80531799 and/or 80531697 for LRRTM1. 122296586 for PARP. 98340854 and/or 98340751 for ZAP70. 29886870 and or 29886944 for miR193 respectively and combination thereof; and/or 2) the hypomethylation of at least one of the CpG/CpG island of SEQ ID NO: 63 for miR296, SEQ ID NO: 65 for TERT, preferably the CpG/CpG island having the following coordinates: 57392374 and or 57392363 for miR296, 1279758 and or 1279775 and/or 1279747 for TERT respectively.

According to a further preferred embodiment, phase (iii) of measuring the epigenetic modifications of set (3)—KIF1A, LRRTM1, ZAP70, miR193, miR296, hTERT—involves measuring 1) the hypermethylation of at least one of the CpG/CpG island of SEQ ID NO: 59 for KIF1A, SEQ ID NO: 64 for LRRTM1, SEQ ID NO: 56 for ZAP70, SEQ ID NO: 57 for miR193, more preferably the hypermethylation of the CpG/CpG island having the following coordinates: 241759686, 241759681, 241759651, 241759621 for KIF1A, 80531799 and/or 80531697 for LRRTM1, 98340854 and/or 98340751 for ZAP70, 29886944 and/or 29886870 for miR193 respectively and any combination thereof; and/or 2) the hypomethylation of at least one of the CpG/CpG island of SEQ ID NO: 63 for miR296, SEQ ID NO: 65 for TERT, more preferably the hypomethylation of the CpG/CpG island having the following coordinates: 57392374 and or 57392363 for miR296, 1279758 and or 1279775 and/or 1279747 for TERT respectively.

According to a further preferred embodiment phase (iii) of measuring the epigenetic modifications of set (4)—KIF1A, LRRTM1, FLI1, LINC00599, PARP15, ZAP70, miR193, miR296, GP1BB, hTERT—involves measuring 1) the hypermethylation of at least one of the CpG/CpG island of SEQ ID NO: 59 for KIF1A, SEQ ID NO: 64 for LRRTM1, SEQ ID NO: 61 for FLI1, SEQ ID NO: 60 for LINC00599, SEQ ID NO: 53 for PARP15, SEQ ID NO: 56 for ZAP70, SEQ ID NO: 57 for miR193, more preferably the hypermethylation of the CpG/CpG island having the following coordinates: 241759686, 241759681, 241759651, 241759621 for KIF1A, 80531799 and/or 80531697 for LRRTM1, 128564158 and/or 128564051 for FLI1, 9760888 for LINC0059, 122296586 for PARP15, 98340854 and/or 98340751 for ZAP70 any combination thereof; and/or 2) the hypomethylation of at least one of the CpG/CpG island of SEQ ID NO: 63 for miR296, SEQ ID NO: 62 for GP1BB, SEQ ID NO: 65 for TERT, more preferably the hypomethylation of the CpG/CpG island having the following coordinates: 57392374 and/or 57392363 for miR296, 19710956 and/or 19710946 for GP1 BB, 1279758 and or 1279775 and/or 1279747 for TERT.

According to a further preferred embodiment phase (iii) of measuring the epigenetic modifications of set (5)—EPHX3, KIF1A, LRRTM1, FLI1, ITGA4, LINC00599, NTM, PARP15, ZAP70, miR193, miR296, GP1BB, hTERT—involves measuring 1) the hypermethylation of at least one of the CpG/CpG island of KIF1A, preferably 1-4 CpG/CpG island of KIF1A, more preferably selected from SEQ ID NO: 59, SEQ ID NO: 58 for EPHX3, SEQ ID NO: 64 for LRRTM1, SEQ ID NO: 61 for FLI1, SEQ ID NO: 54 for ITGA4, SEQ ID NO: 60 for LINC00599, SEQ ID NO: 55 for NTM, SEQ ID NO: 53 for PARP15, SEQ ID NO: 56 for ZAP70, SEQ ID NO: 57 for miR193, and/or 2) the hypomethylation of at least one of the CpG/CpG island of SEQ ID NO: 63 for miR296, SEQ ID NO: 62 for GP1 BB, SEQ ID NO: 65 for human TERT.

All the sequences disclosed in the present patent application are listed in Table I and the CpGs/CpG islands for each region are in bold. Sequences showing 80-99.9% identity with these sequences have to be considered part of the disclosure.

In general, for the amplification step, a locus-specific amplicon library is preferably generated, more preferably a locus-specific bisulfite amplicon library. To this end is advisable to use a platform selected from: MiSEQ, NEXT500 or MiniSEQ—Illumina, IonTorrent, Pacific Biosciences and 454 GSJunior platform.

In the context of the present invention, IonTorrent is one of next-generation sequencing machine that utilizes massively parallel sequencing technologies to generate thousands of megabases of sequence information by semiconductor chips. In the context of the present invention, Illumina MiSEQ, NEXT500 or MiniSEQ are next-generation sequencing machines, which utilize sequence by synthesis chemistry to perform parallel sequencing of billions of DNA fragments in parallel with high precision, minimizing incorporation bias and reducing raw error rates compared to other technologies, especially for homopolymers. In any case, any method to obtain the same purpose has to be considered part of the present disclosure.

According to a preferred embodiment, the amplification steps involves a first step of amplification—a template specific amplification—and a second round of amplification allowing the barcoding of the template-specific amplicons obtained from the first amplification step.

The first amplification step uses preferably a multiplex strategy, preferably by using tagged primer pairs and a DNA polymerase, preferably the Phusion™ U DNA polymerase (FIG. 1-A).

Preferably, the amplification conditions for this first amplification step are the following:
1) At least one step at about 98° C. for about 2 min;
2) At least 1 cycle at about 98° C. for about 10 sec, about 62° C. for about 2 min, about 72° C. for about 1 min;
3) At least 30-40, preferably about 35 cycles, at about 98° C. for about 10 sec, about 62° C. for about 40 sec and about 72° C. for about 20 sec.

A final extension step at about 72° C. for about 5 min is preferably added at the end of the last cycle.

By using multiplex conditions several regions of interest of the genes can be amplified together in order to minimize costs and hands on time. This means that at least one region of interest for at least one gene can be amplified (amplicon) at the same time by using multiplex conditions. For the purpose of the present invention, the multiplex allows to amplify at least one sequence of at least one genomic DNA region comprising at least one CpG/CpG island of at least one gene selected from: PARP15, ITGA4, LRRTM1, human TERT, NTM, MIR193a, KIF1A, LINC00599, ZAP70, EPHX3, MIR296, FLI1N, GP1BB and combination thereof, preferably at least one of the following combinations of genes:
(a) PARP15, ITGA4, LRRTM1, human TERT; and/or
(b) NTM, MIR193a, KIF1A; and/or
(c) LINC00599, ZAP70, EPHX3; and/or
(d) MIR296, FLI1N, GP1BB.

According to a preferred embodiment, for the first amplification step—the template specific amplification step—the primer pair is selected from the following tagged primer pairs:
SEQ ID NOs: 1 and 2 and/or SEQ ID NOs: 27 and 28 for amplifying PARP15 preferably with IonTorrent and Illumina platforms respectively; and/or
SEQ ID NOs: 3 and 4 and/or SEQ ID NOs: 29 and 30 for amplifying ITGA4 preferably with IonTorrent and Illumina platforms respectively; and/or
SEQ ID NOs: 5 and 6 and/or SEQ ID NOs: 31 and 32 for amplifying NMT preferably with IonTorrent and Illumina platforms respectively; and/or
SEQ ID NOs: 7 and 8 and/or SEQ ID NOs: 33 and 34 for amplifying ZAP70 preferably with IonTorrent and Illumina platforms respectively; and/or
SEQ ID NOs: 9 and 10 and/or SEQ ID NOs: 35 and 36 for amplifying MIR193A preferably with IonTorrent and Illumina platforms respectively; and/or
SEQ ID NOs: 11 and 12 and/or SEQ ID NOs: 37 and 38 for amplifying EPHX3 preferably with IonTorrent and Illumina platforms respectively; and/or SEQ ID NOs: 13 and 14 and/or SEQ ID NOs: 39 and 40 for amplifying KIF1A preferably with IonTorrent and Illumina platforms respectively; and/or SEQ ID NOs: 15 and 16 and/or SEQ ID NOs: 41 and 42 for amplifying LINC00599, preferably with IonTorrent and Illumina platforms respectively; and/or SEQ ID NOs: 17 and 18 and/or SEQ ID NOs: 43 and 44 for amplifying FLI1, preferably with IonTorrent and Illumina platforms respectively; and/or SEQ ID NOs: 19 and 20 and/or SEQ ID NOs: 45 and 46 for amplifying GP1BB, preferably with IonTorrent and Illumina platforms respectively; and/or SEQ ID NOs: 21 and 22 and/or SEQ ID NOs: 47 and 48 for amplifying MIR296, preferably with IonTorrent and Illumina platforms respectively; and/or SEQ ID NOs: 23 and 24 and/or SEQ ID NOs: 49 and 50 for amplifying LRRTM1, preferably with IonTorrent and Illumina platforms respectively; and/or SEQ ID NOs: 25 and 26 and/or SEQ ID NOs: 51 and 52 for amplifying human TERT, preferably with IonTorrent and Illumina platforms respectively.

Any combination of primer pairs can be used for each platform depending on the regions of the genes to amplify.

Each tagged primer pair comprises two primers (a forward and a reverse primer) for amplifying the region of interest. Each primer of the pair is a fusion primer comprising 1) a template specific portion hybridizing the specific sequence to amplify (3'-portion); and 2) a universal sequence (5'-portion) that does not have a complementary region in the genome (does not hybridize with any sequence in the genome). Therefore, the universal sequence is fused to a sequence targeting the template-specific sequence ends—that preferably define the boundaries of the amplicon.

In the context of the present invention, "universal sequence" is a sequence that does not have a complementary region in the genome, in other words it does not hybridize with any sequence in the genome. In particular, this sequence is recognized by a second primer combination carrying Illumina or IonTorrent adaptors and/or indexes.

The two forward primers or the two reverse primers for each region to be amplified for the platforms IonTorrent and Illumina, for example SEQ ID NO: 1 and SEQ ID NO: 27, have preferably the same 3' end (because this end is the template specific end) and a different 5' end depending of the used platform.

According to a preferred embodiment, in order to maintain the sequencing directionality, different universal sequences (tails) have to be designed for the two fusion primers of the first amplification step (in FIG. 1-A are named Univ-A and Univ-B ends of each amplicon). Preferably, after PCR, multiplex amplification products can be combined, more preferably the amplification products of following set of genes are combined (a)-(b) and (c)-(d) for purification with magnetic beads.

The first amplification products (template specific), preferably the multiplex amplification products named amplicons, and/or the combinations are preferably purified, after the amplification step, preferably by using SPRI-AMPure XT. Moreover, they can be also quantified, after purification, preferably with the FluorometerQuantus™ or Qubit™ or similar.

The amplicons, eventually after purification and or quantification, are used as template, preferably in an amount of about 100 ng, for a second round of amplification. This second round is for barcoding the sample and it involves 5-10, preferably about 6 cycles.

This second amplification step is performed preferably in the presence of a further primer pair (forward and reverse). Each primer of the pair comprises starting from the 5' end: 1) an adaptor sequence specific for the specific next generation sequencing platform used, such as Illumina and/or IonTorrent, and/or 2) a samples-specific barcode sequences, such as multiplex identifiers (MIDs) or indexes, and/or 3) a universal liker tag complementary to the universal sequence of the primer pair used in the first amplification step (FIG. 1-A).

In the context of the present invention, "samples-specific barcode sequences or indexes" are short sequence that have been introduced artificially to specific target sequence allowing the identification of each sample (in other words to identify the individual) in parallel sequencing when samples from different individuals undergo to the method. Individual "barcode" sequences are added to each sample so they can be distinguished and sorted during data analysis. This approach is cost and time effective because pooling samples exponentially increases the number of samples analyzed in a single run.

In the context of the present invention, "multiplex identifiers or indexes" are inserted during the second round of amplification and include also adaptors specific for the specific next generation sequencing platform is intended to use, allowing the annealing of target sequences to the chip or the flow cell.

In the context of the present invention, "amplicon library" means a pool of target sequences derived from various samples, which are needed to be sequenced in parallel. Any sequencing technique has to be considered part of the present disclosure.

TABLE I

| SEQ ID NO: 1 | PARP15-forward | GTAATACGACGGTCAGT-GTTGTTTTGAGTTTAGGGGTTT |
|---|---|---|
| SEQ ID NO: 2 | PARP15-reverse | CAGGAAACAGCTATGAC-ACTCAACCCTACTATCCCCTTCC |
| SEQ ID NO: 3 | ITGA4-forward | GTAATACGACGGTCAGT-GAGAGYGTATGGTTTGGGAAG |
| SEQ ID NO: 4 | ITGA4-reverse | CAGGAAACAGCTATGAC-AAAAACRCATCAATCCAACTCT |
| SEQ ID NO: 5 | NMT-forward | GTAATACGACGGTCAGT-GTGTTTGAATTGTYGTTGG |
| SEQ ID NO: 6 | NMT-reverse | CAGGAAACAGCTATGAC-ATATTCCTCCCCCAAATCCA |

TABLE I-continued

| SEQ ID NO: 7 | ZAP70-forward | GTAATACGACGGTCAGT-TATTGTGGATYGGTAGAGTTTTG |
|---|---|---|
| SEQ ID NO: 8 | ZAP70-reverse | CAGGAAACAGCTATGAC-CTCTCACCTCCAACTTCCA |
| SEQ ID NO: 9 | MIR193A-forward | GTAATACGACGGTCAGT-GTGTAATTTTTGGAGGGTTGGGT |
| SEQ ID NO: 10 | MIR193A-reverse | CAGGAAACAGCTATGAC-AAACTAAAACTTTATAAACCAATTAATCC |
| SEQ ID NO: 11 | EPHX3-forward | GTAATACGACGGTCAGT-GGYGATATGTYGGAGTTGGT |
| SEQ ID NO: 12 | EPHX3-reverse | CAGGAAACAGCTATGAC-CCAACRAAAAATCRCTCAAA |
| SEQ ID NO: 13 | KIF1A-forward | GTAATACGACGGTCAGT-ATAAATTAGTTGGYGATTGGAGTT |
| SEQ ID NO: 14 | KIF1A-reverse | CAGGAAACAGCTATGAC-CCCCRCATAAACACTAACATAAA |
| SEQ ID NO: 15 | LINC00599-forward | GTAATACGACGGTCAGT-GTTAAGAATGGGGTTGGTTGAGTAT |
| SEQ ID NO: 16 | LINC00599-reverse | CAGGAAACAGCTATGAC-CCCTATCTATCACAAACTACACACCTC |
| SEQ ID NO: 17 | FLI1-forward | GTAATACGACGGTCAGT-ATAGGGGAGTGAGGGTAGG |
| SEQ ID NO: 18 | FLI1-reverse | CAGGAAACAGCTATGAC-CCCRCCRCTTACCTTAATA |
| SEQ ID NO: 19 | GP1BB-forward | GTAATACGACGGTCAGT-TTGTTTTGGTGATAGGAGAATAATG |
| SEQ ID NO: 20 | GP1BB-reverse | CAGGAAACAGCTATGAC-ACCTAACCAAAAATAACCCAAAAAC |
| SEQ ID NO: 21 | MIR296-forward | GTAATACGACGGTCAGT-GGGTATTGGGGAATGGTGA |
| SEQ ID NO: 22 | MIR296-reverse | CAGGAAACAGCTATGAC-CRAAAACCCCAAACCTAACA |
| SEQ ID NO: 23 | LRRTM1-forward | GTAATACGACGGTCAGT-GTTTGGTGGAGGGAAGGAGT |
| SEQ ID NO: 24 | LRRTM1-reverse | CAGGAAACAGCTATGAC-TAACCRACRCCACCTTTTAC |
| SEQ ID NO: 25 | hTERT-forward | GTAATACGACGGTCAGT-GGTTTTTGTATTTATTTTTGTGGTT |
| SEQ ID NO: 26 | hTERT-reverse | CAGGAAACAGCTATGAC-CCAACTTCCTCAAACCCTATTTAA |
| SEQ ID NO: 27 | PARP15-forward | TCGTCGGCAGCGTCAGATGTGTATAAGAGACAGNNNN-GTTGTTTTGAGTTTAGGGGTTT |
| SEQ ID NO: 28 | PARP15-reverse | GTCTCGTGGGCTCGGAGATGTGTATAAGAGACAGNNNN-ACTCAACCCTACTATCCCCTTCC |
| SEQ ID NO: 29 | ITGA4-forward | TCGTCGGCAGCGTCAGATGTGTATAAGAGACAGNNNN-GAGAGYGTATGGTTTGGGAAG |
| SEQ ID NO: 30 | ITGA4-reverse | GTCTCGTGGGCTCGGAGATGTGTATAAGAGACAGNNNN-AAAAACRCATCAATCCAACTCT |
| SEQ ID NO: 31 | NMT-forward | TCGTCGGCAGCGTCAGATGTGTATAAGAGACAGNNNN-GTGTTTGAATTGTYGTTGG |
| SEQ ID NO: 32 | NMT-reverse | GTCTCGTGGGCTCGGAGATGTGTATAAGAGACAGNNNN-ATATTCCTCCCCCAAATCCA |

TABLE I-continued

| | | |
|---|---|---|
| SEQ ID NO: 33 | ZAP70-forward | TCGTCGGCAGCGTCAGATGTGTATAAGAGACAGNNNN-TATTGTGGATYGGTAGAGTTTTG |
| SEQ ID NO: 34 | ZAP70-reverse | GTCTCGTGGGCTCGGAGATGTGTATAAGAGACAGNNNN-CTCTCACCTCCAACTTCCA |
| SEQ ID NO: 35 | MIR193A-forward | TCGTCGGCAGCGTCAGATGTGTATAAGAGACAGNNNN-GTGTAATTTTTGGAGGGTTGGGT |
| SEQ ID NO: 36 | MIR193A-reverse | GTCTCGTGGGCTCGGAGATGTGTATAAGAGACAGNNNN-AAACTAAAACTTTATAAACCAATTAATCC |
| SEQ ID NO: 37 | EPHX3-forward | TCGTCGGCAGCGTCAGATGTGTATAAGAGACAGNNNN-GGYGATATGTYGGAGTTGGT |
| SEQ ID NO: 38 | EPHX3-reverse | GTCTCGTGGGCTCGGAGATGTGTATAAGAGACAGNNNN-CCAACRAAAAATCRCTCAAA |
| SEQ ID NO: 39 | KIF1A-forward | TCGTCGGCAGCGTCAGATGTGTATAAGAGACAGNNNN-ATAAATTAGTTGGYGATTGGAGTT |
| SEQ ID NO: 40 | KIF1A-reverse | GTCTCGTGGGCTCGGAGATGTGTATAAGAGACAGNNNN-CCCCRCATAAACACTAACATAAA |
| SEQ ID NO: 41 | LINC00599-forward | TCGTCGGCAGCGTCAGATGTGTATAAGAGACAGNNNN-GTTAAGAATGGGGTTGGTTGAGTAT |
| SEQ ID NO: 42 | LINC00599-reverse | GTCTCGTGGGCTCGGAGATGTGTATAAGAGACAGNNNN-CCCTATCTATCACAAACTACACACCTC |
| SEQ ID NO: 43 | FLI1-forward | TCGTCGGCAGCGTCAGATGTGTATAAGAGACAGNNNN-ATAGGGGAGTGAGGGTAGG |
| SEQ ID NO: 44 | FLI1-reverse | GTCTCGTGGGCTCGGAGATGTGTATAAGAGACAGNNNN-CCCRCCRCTTACCTTAATA |
| SEQ ID NO: 45 | GP1BB-forward | TCGTCGGCAGCGTCAGATGTGTATAAGAGACAGNNNN-TTGTTTTGGTGATAGGAGAATAATG |
| SEQ ID NO: 46 | GP1BB-reverse | GTCTCGTGGGCTCGGAGATGTGTATAAGAGACAGNNNN-ACCTAACCAAAATAACCCAAAAC |
| SEQ ID NO: 47 | MIR296-forward | TCGTCGGCAGCGTCAGATGTGTATAAGAGACAGNNNN-GGGTATTGGGGAATGGTGA |
| SEQ ID NO: 48 | MIR296-reverse | GTCTCGTGGGCTCGGAGATGTGTATAAGAGACAGNNNN-CRAAACCCCAAACCTAACA |
| SEQ ID NO: 49 | LRRTM1-forward | TCGTCGGCAGCGTCAGATGTGTATAAGAGACAGNNNN-GTTTGGTGGAGGGAAGGAGT |
| SEQ ID NO: 50 | LRRTM1-reverse | GTCTCGTGGGCTCGGAGATGTGTATAAGAGACAGNNNN-TAACCRACRCCACCTTTTAC |
| SEQ ID NO: 51 | hTERT-forward | TCGTCGGCAGCGTCAGATGTGTATAAGAGACAGNNNN-GGTTTTTGTATTTATTTTTGTGGTT |
| SEQ ID NO: 52 | hTERT-reverse | GTCTCGTGGGCTCGGAGATGTGTATAAGAGACAGNNNN-CCAACTTCCTCAAACCCTATTTAA |
| SEQ ID NO: 53 | PARP15 amplicon 122296564-122296725 | CGACCCCCAGAGAACTTATGCACGGAGTTGCAGGTGTTACTTCCAGAGCCGGACCGAGATC GGGAGGCGGGGAGCCGTGCTGCCGGCCGG GAACCGTGGGGCGCGGAAGGCCTCCCGGC GCTCTTCCTCCCGGAGTATGGTGAGGAGCGCGGGGGGACGGGTGCG |
| SEQ ID NO: 54 | ITGA4 amplicon | TCACGTCTGAGCGCACCGTGCACGTGTCTCGCTTTAGGCTCCTAGTGGGTGCGCCCACTGC |

TABLE I-continued

| | | |
|---|---|---|
| | 182322887-<br>182323053 | CAACTGGCTCGCCAACCGCTTCAGTGATCAAT<br>CCCCGGGGCGATTTACAGATGCAGGATCGGA<br>AAGAATCCCCGGCCAGACGTGCGAACAGCTC<br>CAGCTGGGTGAGTTGG |
| SEQ ID NO: 55 | NTM<br>amplicon<br>131781042-<br>131781185 | GAAGCGGCTCCTGAGACGCGCCCACACCTT<br>TCACCTGCCGCGCGCTTCCCCCTCCTCGGC<br>CACCTTCCCGGCGGAAGCAGCGAGGAGGG<br>AGCCCCCTTTGGCCGTCCTCCGTGGAACCG<br>GTTTTCCGAGGCTGGCAAAAGCCGA |
| SEQ ID NO: 56 | ZAP70<br>amplicon<br>98340750-<br>98340885 | GCGAGTTCTACTCGCGCGACCCCGACGGGC<br>TGCCCTGCAACCTCGCAAGCCGTGCAACC<br>GGCCGTCGGGCCTCGAGCCGCAGCCGGGG<br>GTCTTCGACTGCCTGCGAGACGCCATGGTG<br>CGTGACTACCGTGCGCCA |
| SEQ ID NO: 57 | MIR193A<br>amplicon<br>29886860-<br>29887068 | TTGGAGCCCGCGACCCCGAGGTCGGGCGGG<br>GCGGTGGACTTTCCCGGGGAACGCCGCCT<br>GAGGGACACCCAGAGCTTCGGCGGAGCGG<br>AGCGCGGTGCACAGAGCCGGCGACCGGAC<br>CCAGCCCCGGGAAGCCCGTCGGGGACGCA<br>CCCCCGAACTCCCGAGGATGGGAGCTGAGGG<br>CTGGGTCTTTGCGGGGCGAGATGAGGGTGTC<br>GGATC |
| SEQ ID NO: 58 | EPHX3<br>amplicon<br>15342826-<br>15343049 | GCCGCCGTGGTCCCGGAGCGCGGCGACAT<br>GCCGGAGCTGGTGGTGACCGCGCTGCTGG<br>CGCCGTCGCGCCTGTCCGCTGAAGCTGCTGC<br>GCGCCTTCATGTGGAGCCTGGTGTTCTCGG<br>TGGCGCTGGTGCCCGCGGCGGTCTACGGC<br>TGCATAGCGCTCACGCACGTGCTGTGCCGG<br>CCCCGGCGCGGCTGCTGCGGGCGCCGTCG<br>GAGCGCGTCCCCCGCCTG |
| SEQ ID NO: 59 | KIF1A<br>amplicon<br>241459586-<br>241759727 | TCGGACGCCGCGCAGCCAACCAGCGCC<br>TCGGGAGGGGCGCGGGGCGGTCCGGGCC<br>GGGGGCGCGCAGCCCGTCACGCGGCGGCG<br>CCCGTCACAGCGCAGAGCAGCCGGCGAGCG<br>GCAGCAGCTCCGGGCTCGAGAGCCCGC |
| SEQ ID NO: 60 | LINC00599<br>amplicon<br>9760739-<br>9760890 | ACCGTGGGTCGGCGAGGGCCCGCCAAGGA<br>AGGAGCGACCGACCGAGCCAGGCGCCCTC<br>CGCAGACCTCCGCGCAGCGGCCGCGGGCG<br>CGAGGGGAGGGGTCTGGAGCTCCCCGG<br>CTGCCTGTCCCGCACCGGAGCCCGTGGGG<br>TGGGGAG |
| SEQ ID NO: 61 | FLI1<br>amplicon<br>128564020-<br>128564160 | CTCGCAGGGGGCACGCAGGGAGGGCCCAG<br>GGCGCCAGGGAGGCCGCGCCGGGCTAATC<br>CGAAGGGGCTGCGAGGTCAGGCGGCTGTAACC<br>GGGTCAATGTGTGGAATATTGGGGGCTCG<br>GCTGCAGACTTGGCCAAATGGACG |
| SEQ ID NO: 62 | GP1BB<br>amplicon<br>19710829-<br>19710960 | TGTTGGTGAACGTCGCAGCGGGGTGTCCGAG<br>TGCTCCGTGTGCCCCTGAGAGCGGGTGGGA<br>GCGGAAGCCTGAGCGGCCTGCCGCCTCCG<br>GCCGATAGTGTGCTATCTGCCGCTGCAGCGC<br>GCGTCCGCGCGGC |
| SEQ ID NO: 63 | MIR296<br>amplicon<br>57392355-<br>57392545 | GCCGTGCCGCGCCTCTGCCACAGTCTCCCG<br>TGGGTCCCCACTGCCGGGAGTTTTACCTAC<br>CTCCCACCCTCAGCCACGAGCACCTGCAGG<br>ATGCGGTGCCATCCTCGCCGGTGCCCGCTC<br>CCCTTCCGGAGGCTCTCTCCACCCTCACTG<br>ACGCCTCCTCGGGAAAGCCCCCCGCTCCTTC<br>CCCCGACCTCAC |
| SEQ ID NO: 64 | LRRTM1<br>amplicon<br>80531676-<br>80531807 | GGCGCCGCTCGCCGCTCCCCGCGCCGCCG<br>TCCGCACCTCCCCACCGCCCGCCGCCCGC<br>CGCCCGCCGCCCGCAAAGCATGAGTGAGC<br>CCGCTCTCTGCAGCTGCCCGGGGCGCGAAT<br>GGCAGGCTGTTTCCG |
| SEQ ID NO: 65 | Human TERT<br>amplicon<br>1279743-<br>1279851 | GCTGCGGTGGCTGCGGTGACCCCGTCATCT<br>GAGGAGAGTGTGGGGTGAGGTGGACAGAG<br>GTGTGGCATGAGGATCCCGTGTGCAACACA<br>CATGCGGCCAGGAACCCCGTT |

TABLE I-continued

| SEQ ID NO: 66 | IonTorrent A | CCATCTCATCCCTGCGTGTCTCCGACTCAG-CTAAGGTAACGAT-GTAATACGACGGTCAGT |
|---|---|---|
| SEQ ID NO: 67 | IonTorrent P | CCTCTCTATGGGCAGTCGGTGAT-CAGGAAACAGCTATGAC |
| SEQ ID NO: 68 | P5 index 503 | AATGATACGGCGACCACCGAGATCTACAC-TATCCTCT-TCGTCGGCAGCGTCAGATGTGTATAAGAGACAG |
| SEQ ID NO: 69 | P7 index 702 | CAAGCAGAAGACGGCATACGAGAT-CTAGTACG-GTCTCGTGGGCTCGGAGATGTGTATAAGAGACAG |
| SEQ ID NO: 70 | Forward Universal A | GTAATACGACGGTCAGT |
| SEQ ID NO: 71 | reverse Universal B | CAGGAAACAGCTATGAC |

Table II summarize several information on the genes analysed in the present method, the mapping information and the size of the amplified genomic region the reference of the sequence (NM reference on NCBI) and the number of the CpGs/CpG islands.

TABLE II

| Gene | Map | RefSEQ | Position | UCSC h19 coordinates | Amplicon length | Position respect to TSS | Number of interrogated CpG | Imprinting status |
|---|---|---|---|---|---|---|---|---|
| ZAP70 | 2q11.2 | NM_001079 | Exon 3 | Chrom 2 + strand: 98340750-98340885 | 180 | +10705 | 21 | No |
| GP1BB | 22q11.21 | NM_000407 | Exon 1 | Chrom 22 strand+: 19710829-19710960 | 192 | +315 | 18 | No |
| KIF1A | 2q37.3 | NM_001244008 | Exon 1 | Chrom 2 strand−: 241759586-241759727 | 189 | −8 | 28 | No |
| PARP15 | 3q21.1 | NM_00111352 | Exon 1 | Chrom 3 + strand: 122296564-122296725 | 206 | +93 | 19 | No |
| ITGA4 | 2q31.3 | NM_000885 | Exon 2 | Chrom 2 + strand: 182322887-182323053 | 214 | +912 | 14 | No |
| NTM | 11q25 | NM_016522 | Exon 1 | Chrom 11 + strand: 131781042-131781185 | 190 | +62 | 15 | Yes, Maternal, no SNP |
| MIR193A | 17q11.2 | NR_029710 | Promoter | Chrom 17 strand+: 29886860-29887068 | 256 | −178 | 26 | No |
| MIR137HG | 1p21.3 | NR_046105 | Exon 1 | Chrom 1 strand−: 98511645-98511814 | 216 | +136 | 18 | No |
| EPHX3 | 19p13.12 | NM_024794 | Exon 1 | Chrom 19 strand−: 15342826-15343049 | 223 | +215 | 29 | No |
| LINC00599 | 8p23.1 | NR_029668 | Exon 1 | Chrom 8, strand−: 9760739-9760890 | 199 | +69 | 20 | No |
| FLI1 | 11q24.3 | NM_001271010 | Exon 1 | Chrom 11 strand+: 128564020-128564160 | 186 | +187 | 12 | No |
| MIR296 | 20q13.32 | NR_029844 | Exon 1 | Chrom 20 strand−: 57392355-57392545 | 238 | +180 | 15 | Yes, paternal, no SNP |
| LRRTM1 | 2p12 | NM_178839 | Promoter | Chrom 2 strand−: 80531676-80531807 | 179 | −431 | 24 | Yes, paternal, No SNP |
| hTERT | 5p15.33 | NM_198253 | Promoter | Chrom 5 strand−: 1279743-1279851 | 109 | +14976 | 6 | No, SNP at rs 10069690 |

After determining the sequences of the amplicons, preferably according to the disclosure above, the quantitative methylation level measurement is performed using the common tools used for this purpose, preferably selected from: BISMARK, BS-Seeeker2, BISMA, BSPAT, and QUMA. FIG. 1-B summarize a specific embodiment exemplifying the methylation level measurement step, in other words the last phase of the method allowing the determination of the eventual positivity of the sample for HNSCC.

The analysis is based on the fact that bisulfite treatments of nuclei acid sequences converts an unmethylated cytosine (C) to uracil (U), such that uracil (U) is read thymine (T) when the treated nucleic acid is sequenced. This conversion does not affect a methylated C which remains C in the sequence. Therefore, sequencing reads showing C after bisulfite treatments mean a methylated cytosine, instead a T in the sequencing reads after bisulfite treatments mean and unmethylated cytosine.

According to a preferred embodiment, after the sequencing step, a FASTQ file comprising all the sequences obtained from a sample/individual (the reads) are qualitatively filtered by using cloud computing known for this purpose. FASTQ files are generally produced by Next Generation Sequencing runs. Preferably, for Illumina FASTQ a filter of Q30 for 90% of bases is applied. Less stringent filtering is applied for IonTorrent (Q scores are defined as the property that is logarithmically related to the base calling error probability (P)2 as $Q=-10\log_{10} P$. For example, if Phred assigns a Q score of 30 (Q30) to a base, this is equivalent to the probability of an incorrect base call 1 in 1000 times. In this case, the base call accuracy is 99.9%). This filtering step allows to obtain high quality sequences. After the filtering step the high quality sequences are preferably converted in a FASTA format and eventually trimmed, preferably 25 base pairs, at one and/or both ends in order to eliminate the primer sequence.

The sequences, preferably the high-quality sequences, obtained for each region amplified, are analyzed for the quantitative methylation level measurement by using the common tools used for this purpose, preferably selected from: BISMARK, BS-Seeeker2, BISMA, BSPAT, and QUMA. Preferably, the FASTA for each region amplified is uploaded on this tool.

These tools compare the wild type sequence and the sequence after bisulfite treatment and give a quantitative measurement of the methylation level. Therefore, these tools allow the measurement of the methylation level for the CpGs/CpG islands falling in each amplified region.

Preferably the reference sequences to upload for every sequence alignment needed by these tools are selected from: SEQ ID NO: 53-65.

Preferably, the hypomethylation value obtained for the hypomethylated CpG reported above of the hypomethylated genes, preferably selected from: TERT, MIR296 and GP1 BB, is inverted as follows: r=1−x, wherein x is the obtained hypomethylation value and r is the value to be included in the linear discriminant analysis.

According to a preferred embodiment, the methylation level data can be analyzed by using a Linear Discriminat Analysis, preferably selecting at least one, preferably all, CpG selected from: 19710956 for GP1BB; 98340854 for ZAP70; 241759621 for KIF1A; 1279758 for TERT; 80531799 for LRRTM1; 131781167 for NTM; 29886944 for MIR193; 122296586 for PARP15; 182322902 for ITGA4; 128564158 for FLI1; 9760888 for LINC0059; 15342885 for EPHX3; and 57392374 for MIR296.

Preferably, to quantify the methylation level of more than one sequence in order to obtain a total methylation level a multiclass Linear Discriminat Analysis (LDA) is preferably used. This means that, for example, when the CpG methylation level of at least one genomic region of more than one gene of interest, such as the set of genes disclosed above, is measured it is advisable to use this algorithm.

According to method of the present invention, the Linear Discriminant function that weighs the contribution of each methylated CpG is calculated by using the following formula:

$$y(r_i)=K+\Sigma c_i * r_i$$

In particular, the discriminant coefficient for each epigenetic modification (methylation) is based on the number and the type of genomic regions used during the analysis.

The discriminant coefficient ($c_i$) is calculated taking into consideration the levels (rates) of each methylation analysed in such way that the difference between positive and negative samples is maximized.

The constant (K) is a fixed number that is added to the discriminant function and is calculated in such way that the difference between positive and negative samples is maximized.

The final value of y is calculated after adding the constant to the summary of the product between the threshold of the methylation level for each at least one CpG/CpG island and the respective coefficient.

For a correct grouping of each sample, a threshold that discriminates between positive and N negative samples is preferably, but not limited to, calculated through a ROC curve analysis.

Values above certain y are to be considered positive.

According to a preferred embodiment, by using the Linear Discriminat Analysis and a ROC, a sample is considered HNSCC positive if:
  (a) using the combination of Human TERT and KIF1A—when y exceeds the threshold of −0.5306765 (AUC: 0.924) with sensitivity of 0.914 and 1-specificity of 0.123); and/or
  (b) using the combination of LRRTM1, PARP15, ZAP70, miR193, miR296, hTERT—when y exceeds the threshold of −0.1582287 (AUC: 0.962) with sensitivity of 0.944 and 1-specificity of 0.085; and/or
  (c) KIF1A, LRRTM1, ZAP70, miR193, miR296, hTERT—when y exceeds the threshold of −0.1258801 (AUC: 0.962) with sensitivity of 0.917 and 1-specificity of 0.07; and/or
  (d) KIF1A, LRRTM1, FLI1, LINC00599, PARP15, ZAP70, miR193, miR296, GP1BB, hTERT—when y exceeds the threshold of 0.4430684 (AUC: 0.970) with sensitivity of 0.972 and 1-specificity of 0.056; and/or
  (e) EPHX3, KIF1A, LRRTM1, FLI1, ITGA4, LINC00599, NTM, PARP15, ZAP70, miR193, miR296, GP1BB, hTERT—when y exceeds the threshold of 1.0582872 (AUC: 0.971) with sensitivity of 0.917 and 1-specificity of 0.

The linear discriminant analysis (LDA) generates a score that weighted the at least one, preferably all, CpG selected from: 19710956 for GP1 BB; 98340854 for ZAP70; 241759621 for KIF1A; 1279758 for TERT; 80531799 for LRRTM1; 131781167 for NTM; 29886944 for MIR193; 122296586 for PARP15; 182322902 for ITGA4; 128564158 for FLI1; 9760888 for LINC0059; 15342885 for EPHX3; and 57392374 for MIR296, from the gene(s) investigated.

This accuracy meets the clinical requirements and thus the method of the invention is ideal to be used in place of and/or alongside the current reference methods.

According to a further aspect of the present invention, the method as disclosed above allow to detect the presence of field cancerization, preferably in surgically resected patients for HNSCC around the site of intervention. In particular, the invention shows that the presence of field cancerization with altered methylation pattern is related to poor prognosis and high risk of recurrence or secondary tumors.

A further aspect of the present invention refers to detect the presence of field cancerization in surgically resected patients for HNSCC around the site of intervention.

The presence of field cancerization with altered methylation pattern is related to poor prognosis and high risk of recurrence or secondary tumors.

A further aspect of the present invention, refers to a kit to determine the presence and/or the risk for HNSCC, preferably HG-SIL and/or OSCC in a biological test sample, preferably containing exfoliating brush of oral mucosa obtained from and individual, who preferably shows OPML or suspect lesions, said kit comprising reagents for sodium bisulfite conversion and a set of oligonucleotides, enzymes and buffers that specifically amplify at least one of the sequences SEQ ID NO: 53-SEQ ID NO: 65 with at least one primer pairs selected from the group consisting of SEQ ID NOs: 1-52 and from SEQ ID NOs: 66-69.

EXAMPLE

For the setting up and the validation phases of the present method, all consecutive patients referred to the Department of Oral Sciences, University of Bologna, from January 2015 to July 2016.

Lesions with an obvious aetiology, such as trauma and infective aphthous ulcerations, were excluded.

All patients presenting with oral lesions that required incisional biopsy to diagnostic purposed underwent also oral brushing of the same lesion.

Oral brushing samples were always picked before incisional biopsy for histological diagnosis and staging of each lesion.

Histological diagnoses were performed following the WHO criteria (Thompson, 2006). Distinction between HG-SIL and LG-SIL was made according to Ljubjana classification 2014 (Gale, Blagus et al. 2014).

A total of 150 oral brushing sample series for the training dataset was composed of:
65 normal healthy donors;
28 OSCC,
1 OSCC with sarcomatoid feature
6 HG-SIL,
35 normal mucosa around the site of intervention of patients previously surgically treated for an OSCC;
The validation dataset was composed of:
2 OSCC;
3 PVL (proliferative verrucous leukoplakia)
14 OLP (oral lichen planus)
1 oral fibroma
20 Healthy normal donors
Oral Brushing Method A cytobrush was used to collect exfoliated cells from oral mucosa.

In OSCC and OPML lesions all surface of lesions was gently brushed repeatedly five times.

Brushing cell collection was always performed before incisional biopsy and without use of any local anaesthetic.

After brushing, each cytobrush sample was placed in a 2 ml tube containing absolute ethanol for cell preservation.
Ethics Statement All clinical investigations have been conducted according to the principles expressed in the Declaration of Helsinki. The study was approved by local Ethics Committee (number of study: 14092, protocol number: 899/CE). All information regarding the human material used in this study was managed using anonymous numerical codes.
DNA Purification DNA from exfoliating brush samples was purified using The MasterPure™ Complete DNA extraction kit (Epicentre, Madison, WI).
Bisulfite Treatment of Genomic DNA Sodium bisulfite treatment of genomic DNA was carried out with the EZ DNA Methylation-Lightning™ Kit (Zymo Research Europe, Freiburg, Germany) according to the manufacturer's protocol.
Amplification Phase For Illumina Platform (MiSEQ), locus-specific bisulfite amplicon libraries were generated multiplexing with tagged primers (see Table 1) using Phusion U DNA polymerase (ThermoFisher) in 25 μl. Illumina platform needs a different method to evaluate amplicons, the Nextera™ approach which requires adaptors at the 5' end as described in Table 1. The insertion of one N or two N in the middle guarantees the minimum complexity for clustering. Barcoding was performed by using Nextera™ index kit.

Cycling conditions for the first template specific PCR were: initial incubation at 98° C. for 2 min followed by 1 cycle of 98° C. 10 sec, 62° C. 2 min, 72° C. 1 min, followed by 35 cycles at 98° C. for 10 s, 62° C. for 40 s and 72° C. for 20 sec. A final extension step at 72° C. for 5 min was added at the end of the last cycle.

Multiplex PCR consisted of:
Multiplex 1 PARP15; ITGA4; LRRTM1; TERT
Multiplex 2 NTM; MIR193a; KIF1A
Multiplex 3 LINC00599; MIR137HG; ZAP70; EPHX3
Multiplex 4 MIR296; FLI1N; GP1BB Reaction conditions for multiplex were: ultrapure water: 8.8 μl, Buffer 5×HF: 5 μl, betaine 5M: 5 μl, dNTPs 10 mM: 0.5, primers 0.1 μM: 1.5 μl, MgCl2 50 mM: 0.5 μl, Phusion U: 0.2 μl, DNA bisulfite treated: 3.5 μl.

Amplification products from multiplex 1-2 and 3-4 were combined and purified using SPRI-AMPure XT (Agencourt-Beckman Coulter, Beverly, MA), quantified with the FluorometerQuantus™ (Promega, Madison, WI) and then employed as template (100 ng) for a second round of PCR (6 cycles).

Sample-specific barcode sequences (Indexes) and universal linker tags (P5/P7 adaptor sequences) were added in this second PCR performed with 6 cycles (98° C. 1 min./98° C. 10 sec./63° C. 30 sec./72° C. 3 min.).

The amplicon library was purified using AgencourtAMPure XP beads (Beckman Coulter, Krefeld, Germany), then quantitated with the FluorometerQuantus™ (Promega, Madison, WI).

The libraries were diluted, pooled at 4 nM and loaded on Nano Flow cell into MiSEQ. Alternatively, for amplicon sequencing experimental design for 454/IonTorrent platforms, the 'Universal Tailed' design requires two sets of primer pairs, used in two successive rounds of PCR.

The first round uses fusion primers targeting the template-specific sequences (defining the boundaries of the amplicons) fused to a universal sequence that will be the target of the second round primers (FIG. 1). In order to maintain sequencing directionality, different universal tails should be designed for the Primer A and Primer B ends of the amplicons (Univ-A and Univ-B on the FIG. 1-A).

In the second round, the Univ-A sequence is targeted by a fusion primer that is tailed by the 454 Sequencing system's Primer A sequence plus an MID sequence to identify the sample; and same for the Univ-B sequence, with Primer B (FIG. 1-A).

As reported in Table I, the forward Universal A Tailed sequence of choice is GTAATACGACGGTCAGT (SEQ ID NO: 70) and the reverse Universal B Tailed sequence of choice is CAGGAAACAGCTATGAC (SEQ ID NO: 71).

In Silico Prediction of CpG Island and Primer Design

In order to identify putative the CpG islands on promoter region of the following genes: ZAP70, ITGA4, KIF1A, PARP15, EPHX3, NTM, LRRTM1, FLI1, MIR193, LINC00599, MIR296, hTERT and GP1BB, genomic sequence as stored on Ensembl genome browser, including 1000 bp upstream the ATG site were employed as query sequence. MethPrimer design were applied to identify CpGs and the best primers of choice (see Table 1).

In the second round of PCR, Universal A and B are recognized to add the specific Adaptors for 454 as follows including Adaptor a+key+MID+Universal A or B:

```
ADPTUNIAFwMID2:
                                           (SEQ ID NO: 72)
CGTATCGCCTCCCTCGCGCCATCAGACGCTCGACA-

GTAATACGACGGTCAGT

ADPTUNIBRvMID5:
                                           (SEQ ID NO: 73)
CTATGCGCCTTGCCAGCCCGCTCAGATCAGACACG-

CAGGAAACAGCTATGAC
```

The same approach was used for IonTorrent/Proton platform as follows:
Primer A: IonXpress 1:
```
                                           (SEQ ID NO: 74)
CCATCTCATCCCTGCGTGTCTCCGACTCAG-

CTAAGGTAACGAT-GTAATACGACGGTCAGT

Primer P:
                                           (SEQ ID NO: 75)
CCTCTCTATGGGCAGTCGGTGAT-CAGGAAACAGCTATGAC
```

Bioinformatic Analysis:

After the end of run, each FASTQ file obtained after the NGS was processed as follows:
  Using Galaxy, the open web-based platform for data intensive biomedical research, load both R1 and R2 FASTQ files.
  Using Pear to merge paired-end reads (R1 Forward and R2 Reverse).
  Using FASTQ Groomer to render FASTQ file compatible with all formats.
  Filtering by Quality: filter for >Q30 at 90% and >100 bp long
  Converting FASTQ file to FASTA
  Trimming from the beginning up to this position 25 bp and remove everything from this position to the end: −25 bp (Ignore lines beginning with these characters)
  Downloading the FASTA file.
  Then using Perl to extract reads from each gene of the analysed sets as follows: (For instance to extract hTERT make the command line: grep-B 1 "GGAGAGTGTGGGGTGAGGTGGATAG" (SEQ ID NO: 76) Name of source file.fasta>Name of Output file.fasta)

Figure 3A:
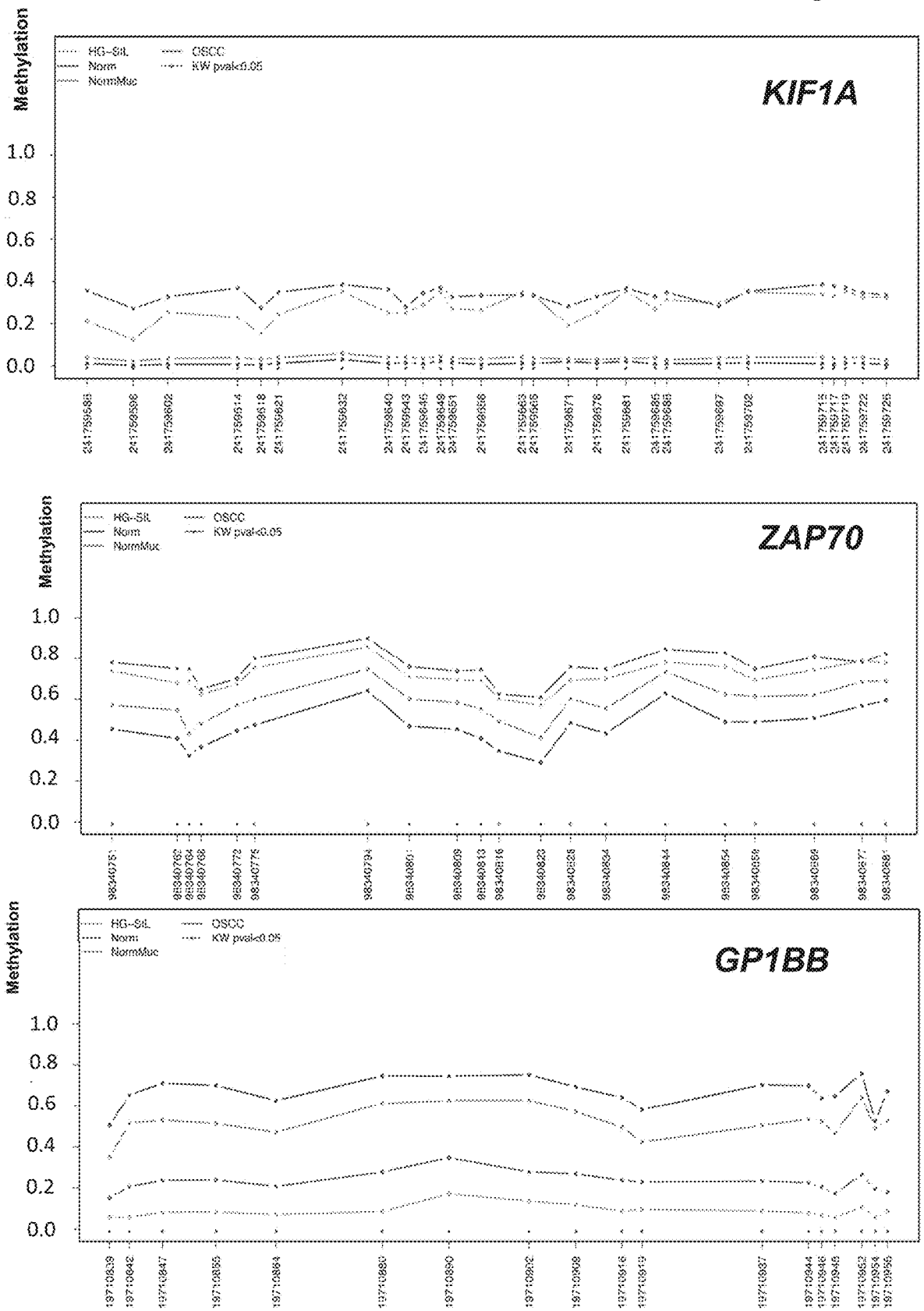
Figure 3B:
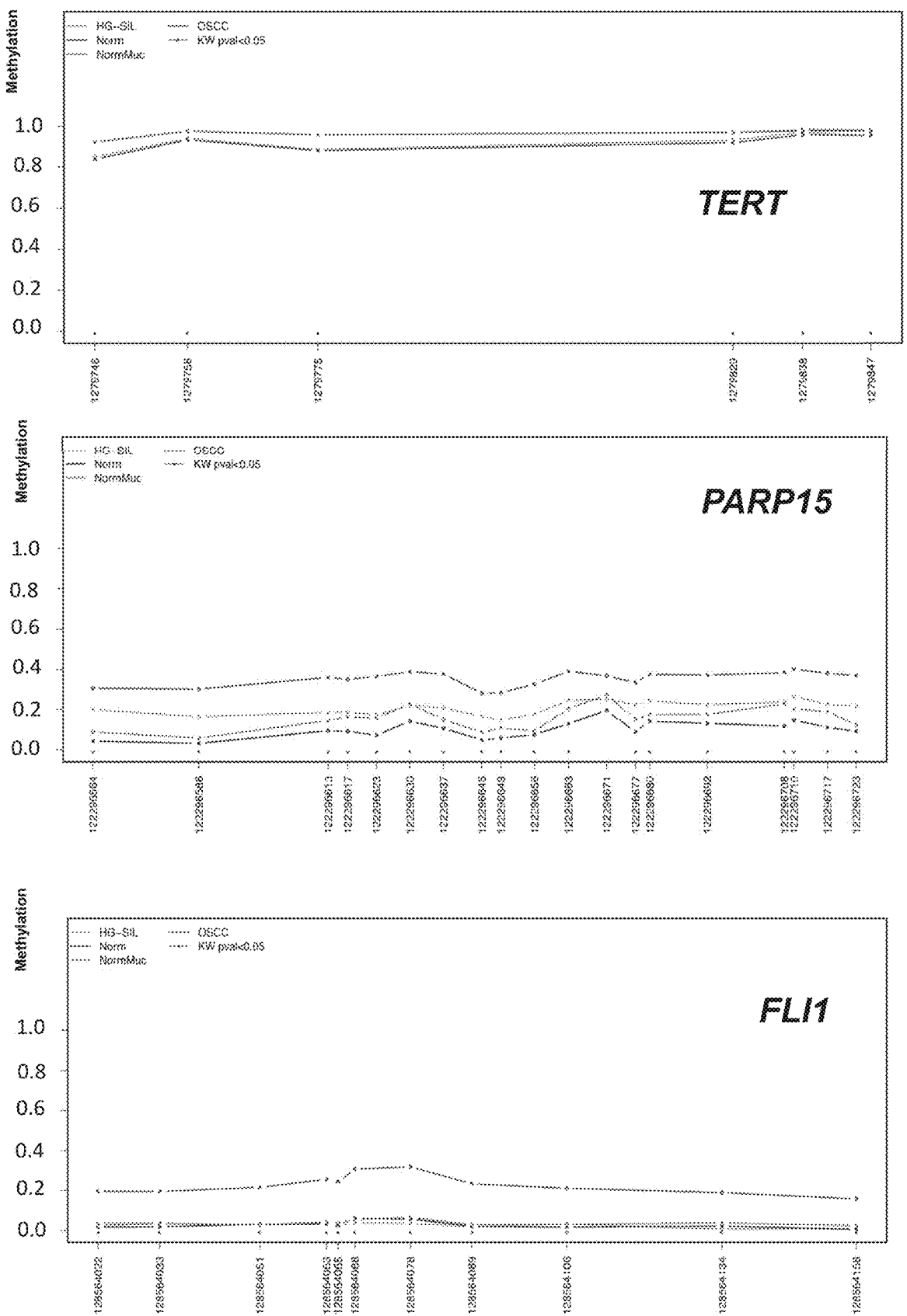
Figure 3C:
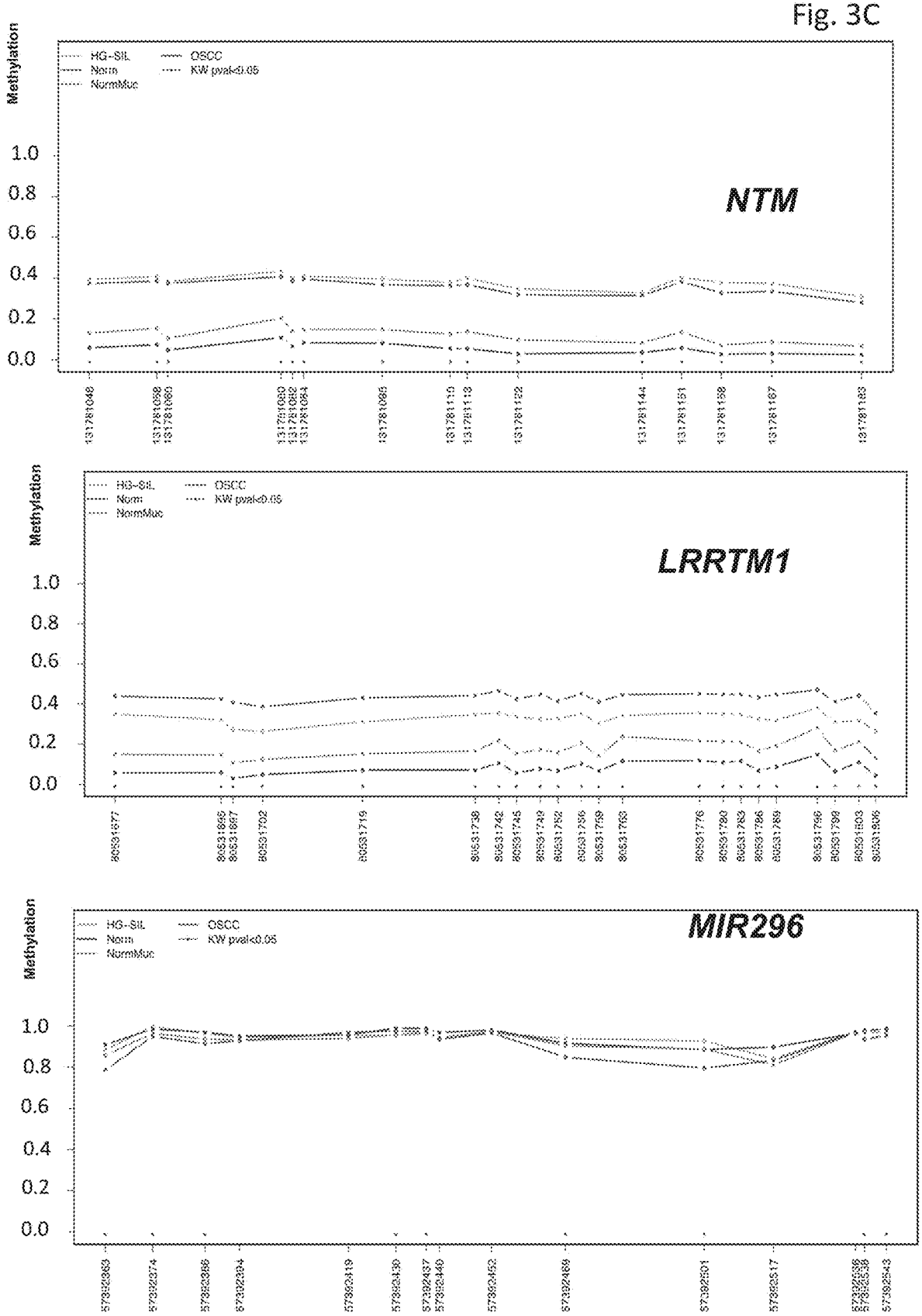

For example for set (e), once extracted all 13 files, load each one to BISMA in order to calculate CpG percentage for each CpG of each gene.
  Creating a Table with CpG methylation level dividing two group, one for normal healthy samples (indicated as class 0), the other one for OSCC and HG-SIL (class 1) for each CpG of each gene; then calculating ROC curve for each of the CpG evaluated and select the best CpG for each gene; FIGS. 3A-C describe ROC analysis and the best three CpG for each gene evaluated.

The behaviour of each CpG respect to their position along the human genome, is graphically pointed out by methylation plotter tool in FIGS. 3A-C.

A table including the best CpGs for each gene has been created wherein class 0=normal donors and class 1=OSCC.

Using this table for LDA discriminant analysis by the tool SPSS (Selecting the following options: variable interval: 0-1; Statistics: not standardized values; Classifications: calculate from group dimension; create a summary Table; Save Discriminant Score).

Then make a ROC curve analysis finding the right threshold.

Example for Set (a)

Set (a) involves the following CpGs: 241759621 for KIF1A and 1279758 for TERT. The Linear Discriminant Analysis calculated the following coefficients:

Canonical Discriminant Function Coefficients

|  | Function 1 |
| --- | --- |
| KIF1A | 5.338 |
| TERT | .707 |
| (Constant) | −.808 |

$y = -0.808 + 5.338*(\text{KIF1A value}) + 0.707*(1-\text{hTERT value})$

By the ROC curve analysis (FIG. 4), large values of the test result variables indicate stronger evidence for a positive actual state.

Area Under the Curve

Test Result Variable(s): Discriminant Scores from Function 1 for Analysis 1

| Area | Std. Error[a] | Asymptotic Sig.[b] | Asymptotic 95% Confidence Interval | |
| --- | --- | --- | --- | --- |
| | | | Lower Bound | Upper Bound |
| .924 | .033 | .000 | .861 | .988 |

Therefore, when the y value exceeds the threshold of −0.5306765, the sample should be considered positive and related to the presence of HG-SIL or OSCC.

Example for Set (b)

Set (b) involves the following genes: LRRTM1 (CpG 80531799), PARP15 (CpG 122296586), ZAP70 (CpG 98340854), MIR193 (CpG 29886944), MIR296 (CpG 57392374), TERT (CpG 1279758).

In this case, the Linear Discriminant Analysis calculated the following coefficients:
Canonical Discriminant Function Coefficients

|  | Function 1 |
|---|---|
| LRRTM1 | 2.422 |
| PARP15 | 1.335 |
| ZAP70 | 3.571 |
| MIR193 | 3.073 |
| MIR296 | 4.730 |
| TERT | .165 |
| (Constant) | −3.470 |

Then the algorithm will be the following: y=−3.470+2.422*(LRRTM1 value)+3.073*(miR193 value)+4.730*(1−miR296 value)+0.165*(1−hTERT value)+1.335*(PARP15 value)+3.571*(ZAP70 value).

By the ROC curve analysis (FIG. 4B), larger values of the test result variables indicate stronger evidence for a positive actual state. The positive actual state is 1.
Area Under the Curve
Test Result Variable(s): Discriminant Scores from Function 1 for Analysis 1

| Area | Std. Error$^a$ | Asymptotic Sig.$^b$ | Asymptotic 95% Confidence Interval | |
|---|---|---|---|---|
|  |  |  | Lower Bound | Upper Bound |
| .975 | .019 | .000 | .937 | 1.000 |

Under the nonparametric assumption b. Null hypothesis: true area=0.5
Coordinates of the Curve
Test Result Variable(s): Discriminant Scores from Function 1 for Analysis 1

| Positive if Greater Than or Equal To$^a$ | Sensitivity | 1-Specificity |
|---|---|---|
| −.1924607 | .971 | .077 |

The smallest cutoff value is the minimum observed test value minus 1, and the largest cutoff value is the maximum observed test value plus 1. All the other cutoff values are the averages of two consecutive ordered observed test values.

Therefore, when the y value exceeds the threshold of 0.1924607, the sample is considered positive and related to the presence of HG-SIL or OSCC.

Example for Set (c)

Set (c) involves the following genes: KIF1A (CpG 241759621), LRRTM1 (CpG 80531799), ZAP70 (CpG 98340854), MIR193 (CpG 29886944), MIR296 (CpG 57392374), TERT (CpG 1279758).
Canonical Discriminant Function Coefficients

|  | Function 1 |
|---|---|
| KIF1A | 1.744 |
| LRRTM1 | 1.844 |
| ZAP70 | 3.656 |
| MIR193 | 2.852 |
| MIR296 | 5.441 |
| TERT | .228 |
| (Constant) | −3.474 |

By the ROC curve analysis (FIG. 5A), larger values of the test result variables indicate stronger evidence for a positive actual state. The positive actual state is 1.
Area Under the Curve
Test Result Variable(s): Discriminant Scores from Function 1 for Analysis 1

| Area | Std. Error$^a$ | Asymptotic Sig.$^b$ | Asymptotic 95% Confidence Interval | |
|---|---|---|---|---|
|  |  |  | Lower Bound | Upper Bound |
| .973 | .019 | .000 | .936 | 1.000 |

$y$=−3.474+1.844*(LRRTM1 value)+2.852*(miR193 value)+5.441*(1−miR296 value)+3.656*(ZAP70 value)+1.744*(KIF1A value)+0.228*(1−hTERT value)

Therefore, when the y value exceeds the threshold of −0.2394214 (sensitivity: 0.943; 1-specificity: 0.077), the sample should be considered positive and related to the presence of HG-SIL or OSCC.

Example for Set (d)

Set (d) involves the following genes: KIF1A (CpG 241759621), LRRTM1 (CpG 80531799), FLI1 (CpG 128564158), LINC00599 (CpG 9760888), PARP15 (CPG 122296586), ZAP70 (CpG 98340854), MIR193 (CpG 29886944), MIR296 (CpG 57392374), GP1BB (CpG 19710956), hTERT (CpG 1279758).
Canonical Discriminant Function Coefficients

|  | Function 1 |
|---|---|
| KIF1A | 1.585 |
| LRRTM1 | 1.631 |
| ZAP70 | 1.996 |
| MIR193 | .625 |
| MIR296 | 8.743 |
| TERT | −.083 |
| FLI1 | −2.630 |
| LINC0599 | −.443 |
| PARP15 | 1.995 |
| GP1BB | 3.899 |
| (Constant) | −3.977 |

By the ROC curve analysis (FIG. 5B), larger values of the test result variables indicate stronger evidence for a positive actual state. The positive actual state is 1.

Area Under the Curve
Test Result Variable(s): Discriminant Scores from Function 1 for Analysis 1

| Area | Std. Error$^a$ | Asymptotic Sig.$^b$ | Asymptotic 95% Confidence Interval | |
|---|---|---|---|---|
| | | | Lower Bound | Upper Bound |
| .973 | .026 | .000 | .922 | 1.000 |

$y=-3.977-2.630*(FLI1\ value)+3.899*(1-GP1BB\ value)+1.631*(LRRTM1\ value)-0.443*(LINC00599\ value)+0.625*(miR193\ value)+8.743*(1-miR296\ value)+1.995*(PARP15\ value)+1.996*(ZAP70\ value)+1.585*(KIF1A\ value)-0.083*(1-hTERT\ value)$ Therefore, when the y value exceeds the threshold of 0.6760154 (sensitivity: 0.971; 1-specificity: 0.015), the sample should be considered positive and related to the presence of HG-SIL or OSCC.

Example for Set (e)

Set (e) involves the following genes with their CpGs: 19710956 for GP1 BB; 98340854 for ZAP70; 241759621 for KIF1A; 1279758 for TERT; 80531799 for LRRTM1; 131781167 for NTM; 29886944 for MIR193; 122296586 for PARP15; 182322902 for ITGA4; 128564158 for FLI1; 9760888 for LINC0059; 15342885 for EPHX3; and 57392374 for MIR296.

Canonical Discriminant Function Coefficients

| | Function 1 |
|---|---|
| KIF1A | 1.789 |
| ZAP70 | 1.983 |
| GP1BB | 3.801 |
| LRRTM1 | 1.428 |
| TERT | −.265 |
| PARP15 | 2.338 |
| FLI1 | −3.471 |
| NTM | −.637 |
| LINC0599 | −.036 |
| EPHX3 | −.415 |
| ITGA4 | 2.276 |
| MIR193 | .894 |
| MIR296 | 7.938 |
| (Constant) | −3.954 |

By the ROC curve analysis (FIG. 5), larger values of the test result variables indicate stronger evidence for a positive actual state. The actual positive actual state is 1.

Area Under the Curve
Test Result Variable(s): Discriminant Scores from Function 1 for Analysis 1

| Area | Std. Error$^a$ | Asymptotic Sig.$^b$ | Asymptotic 95% Confidence Interval | |
|---|---|---|---|---|
| | | | Lower Bound | Upper Bound |
| .973 | .026 | .000 | .921 | 1.000 |

$y=-3.954-0.415*(EPHX3\ value)-3.471*(FLI1\ value)+3.801*(1-GP1BB\ value)+2.276*(ITGA4\ value)+1.428*(LRRTM1\ value)-0.036*(LINC00599\ value)+0.894*(miR193\ value)+7.938*(1-miR296\ value)-0.637*(NTM\ value)+2.338*(PARP15\ value)+1.983*(ZAP70\ value)+1.789*(KIF1A\ value)-0.265*(1-hTERT\ value)$ Therefore, when the y value exceeds the threshold of 0.8732193 (sensitivity: 0.971; 1-specificity: 0), the sample should be considered positive and related to the presence of HG-SIL or OSCC.

Multiple Range Tests Using the Score from the Combination "e":

A Duncan's Multiple Range Test evaluating the final score of patients from different groups (65 Normal donors, 29 OSCC, 6 HGSIL, 30 distant mucosa in OSCC patients) has been calculated using the combination "e" as follows:

$y=-3.954-0.415*(EPHX3\ value)-3.471*(FLI1\ value)+3.801*(1-GP1BB\ value)+2.276*(ITGA4\ value)+1.428*(LRRTM1\ value)-0.036*(LINC00599\ value)+0.894*(miR193\ value)+7.938*(1-miR296\ value)-0.637*(NTM\ value)+2.338*(PARP15\ value)+1.983*(ZAP70\ value)+1.789*(KIF1A\ value)-0.265*(1-hTERT\ value)$ This test identifies a statistical difference between the OSCC group vs healthy donors and vs contralateral mucosa. Furthermore, multiple range test shows a statistical difference between the HGSIL group and healthy donors and contralateral mucosa:

TABLE II indicating for each group the mean score value:

| pathology | Count | Mean | Homogeneous Groups |
|---|---|---|---|
| Healthy donors | 65 | −1.586 | C |
| Distant mucosa in OSCC patients | 30 | −0.444399 | B |
| OSCC | 29 | 2.66856 | A |
| HG SIL | 6 | 2.71892 | A |

TABLE III indicating the significance for each group comparison:

| Contrast | Sig. | Difference | +/− Limits |
|---|---|---|---|
| OSCC-HG SIL | | −0.0503633 | 0.983538 |
| OSCC-distant mucosa in OSCC patients | * | 3.11296 | 0.571081 |
| OSCC-healthy donors | * | 4.25456 | 0.489711 |
| HG SIL-distant mucosa in OSCC patients | * | 3.16332 | 0.980724 |
| HG SIL-healthy donors | * | 4.30492 | 0.935683 |
| Distant mucosa in OSCC patients-healthy donors | * | 1.1416 | 0.484034 |

* denotes a statistically significant difference.

By these data, Multiple Range Test for LDA-generated scores (combination "e") identifies a significant difference between the OSCC group and healthy donors and contralateral mucosa. Furthermore, multiple range test showed a significant difference between the HGSIL group and healthy donors and contralateral mucosa, demonstrating that OSCC and HGSIL have a different epigenetic behavior than normal donors and normal contralateral mucosa.

Algorithm Validation in an Independent Cohort

Considering the validation dataset, all normal donors were detected under the threshold value, as well as one oral fibroma and 12 out of 14 OLP; on the contrary the remaining two OLP, all PVL and all OSCC were positives as expected.

Kruskal-Wallis test (FIG. 5) showed a significant between-group difference for scores generated with linear discriminant analysis (LDA) (T=78,8587, p<0.05).

The invention claimed is:

1. A method for measuring gene methylation, said method comprising:

(i) obtaining an isolated biological sample from an individual;

(ii) purifying genomic DNA from said sample;

(iii) treating the genomic DNA, with bisulfite;

(iv) amplifying the genomic DNA, after step (iii) by using primer pairs, said primer pairs allowing the amplification of sequences of the genomic DNA region of genes selected from: EPHX3, KIF1A, LRRTM1, FLI1, ITGA4, LINC00599, NTM, PARP15, ZAP70, miR193A, miR296, GP1BB, hTERT and any combination thereof, said sequences comprising CpG and/or CpG islands;

(v) measuring the methylation level of each of the CpG and/or CpG islands falling in the sequences amplified according to the step (iv) and belonging to the following set of genes:
a) KIF1A, LRRTM1, FLI1, LINC00599, PARP15, ZAP70, miR193A, miR296, GP1BB, hTERT; and/or
b) EPHX3, KIF1A, LRRTM1, FLI1, ITGA4, LINC00599, NTM, PARP15, ZAP70, miR193A, miR296, GP1BB and hTERT, and (vi) detecting hypermethylation in the CpG and/or CpG islands falling in the sequence of at least one of the following genes: EPHX3, KIF1A, LRRTM1, FLI1, ITGA4, LINC00599, NTM, PARP15, ZAP70 and miR193A and detecting hypomethylation in the miR296, GP1BB and hTERT genes, wherein said hypermethylation and said hypomethylation are compared to a normal mucosa of a healthy individual, wherein the CpG and/or CpG islands are selected from:
  a CpG/CpG island falling in the genomic region of PARP15 exon 1 SEQ ID NO: 53, wherein the CpG/CpG island is selected from nucleotides in positions: 1, 23, 50, 54, 60, 67, 74, 82, 86, 93, 100, 102, 108, 114, 117, 129, 146, 148, 155 and 161 of SEQ ID NO:53 and combination thereof; and/or
  a CpG/CpG island falling in the genomic region of ITGA4 exon 2 SEQ ID NO: 54, wherein the CpG/CpG island is selected from nucleotides in positions: 4, 12, 16, 22, 29, 51, 70, 76, 93, 99, 118, 130, 138 and 142 of SEQ ID NO:54 and combination thereof; and/or
  a CpG/CpG island falling in the genomic region of NTM exon 1 SEQ ID NO: 55, wherein the CpG/CpG island is selected from nucleotides in positions: 5, 17, 19, 38, 40, 42, 57, 69, 72, 81, 103, 110, 118, 126 and 142 of SEQ ID NO:55 and combination thereof; and/or
  a CpG/CpG island falling in the genomic region of ZAP70 exon 3 SEQ ID NO: 56, wherein the CpG/CpG island is selected from nucleotides in positions: 2, 13, 15, 17, 23, 26, 45, 52, 60, 63, 67, 74, 79, 85, 95, 105, 110, 120, 128 and 132 of SEQ ID NO:56 and combination thereof; and/or
  a CpG/CpG island falling in the genomic region of MIR193A promoter SEQ ID NO: 57, wherein the CpG/CpG island is selected from nucleotides in positions: 9, 11, 16, 22, 26, 31, 44, 51, 54, 77, 80, 85, 90, 92, 105, 108, 112, 124, 133, 142, 149, 156, 186, 190 and 204 of SEQ ID NO:57 and combination thereof; and/or
  a CpG/CpG island falling in the genomic region of EPHX3 exon 1 SEQ ID NO: 58, wherein the CpG/CpG island is selected from nucleotides in positions: 3, 6, 14, 19, 21, 24, 32, 48, 50, 59, 62, 65, 67, 74, 88, 90, 116, 122, 132, 134, 137, 144, 161, 164, 175, 181, 184, 186, 195, 199, 202, 205, 210, 212 and 219 of SEQ ID NO:58 and combination thereof; and/or
  a CpG/CpG island falling in the genomic region of KIF1A exon 1 SEQ ID NO: 59, wherein the CpG/CpG island is selected from nucleotides in positions: 2, 6, 9, 11, 13, 26, 31, 40, 42, 47, 52, 57, 63, 65, 72, 76, 78, 81, 84, 88, 96, 107, 110, 114, 126, 132 and 140 of SEQ ID NO:59 and combination thereof; and/or
  a CpG/CpG island falling in the genomic region of LINC00599 exon 1 SEQ ID NO: 60, wherein the CpG/CpG island is selected from nucleotides in positions: 3, 10, 13, 21, 35, 39, 43, 52, 59, 69, 71, 76, 80, 82, 86, 88, 114, 127, 132 and 139 of SEQ ID NO:60 and combination thereof; and/or
  a CpG/CpG island falling in the genomic region of FLI1 exon 1 SEQ ID NO: 61, wherein the CpG/CpG island is selected from nucleotides in positions: 3, 14, 32, 44, 46, 49, 59, 70, 87, 116 and 140 of SEQ ID NO:61 and combination thereof; and/or
  a CpG/CpG island falling in the genomic region of GP1BB exon 1 SEQ ID NO: 62, wherein the CpG/CpG island is selected from nucleotides in positions: 11, 14, 19, 27, 36, 51, 67, 74, 81, 88, 91, 109, 117, 119, 121, 125, 127 and 129 of SEQ ID NO:62 and combination thereof; and/or
  a CpG/CpG island falling in the genomic region of MIR296 exon 1 SEQ ID NO: 63, wherein the CpG/CpG island is selected from nucleotides in positions: 3, 8, 10, 29, 45, 77, 94, 106, 109, 116, 127, 152, 160, 172 and 183 of SEQ ID NO:63 and combination thereof; and/or
  a CpG/CpG island falling in the genomic region of LRRTM1 promoter SEQ ID NO: 64, wherein the CpG/CpG island is selected from nucleotides in positions: 3, 6, 10, 13, 20, 22, 25, 28, 32, 45, 49, 52, 56, 59, 63, 66, 70, 89, 106, 111, 113 and 131 of SEQ ID NO:64 and combination thereof; and/or
  a CpG/CpG island falling in the genomic region of TERT (hTERT) promoter SEQ ID NO: 65, wherein the CpG/CpG island is selected from nucleotides in positions: 5, 14, 23, 77, 94 and 106 of SEQ ID NO:65 and combination thereof.

2. The method according to claim 1, wherein the biological sample is selected from: a brushing from oral mucosa or a DNA buccal swab, plasma, saliva or any sample containing epithelial cells.

3. The method according to claim 1, wherein the amount of genomic DNA undergoing step (iii) ranges from 50 ng to 10 µg.

4. The method according to claim 1, wherein the bisulfite treatment involves a DNA denaturation step and a step of reacting said denaturated DNA with an amount of bisulfite ranging from 2.3 to 3.6 M at a temperature ranging from 45 to 60° C., for at least one hour.

5. The method according to claim 1, wherein the amplification step (iv) involves 1) a first template-specific amplification step to amplify the sequences of the genomic DNA region; and 2) a second amplification step for barcoding the template-specific amplification products and sample identification.

6. The method according to claim 5, wherein the template-specific amplification step is performed using a multiplex strategy.

7. The method according to claim 5, wherein the template-specific amplification step is performed using primer pairs, said primer pairs comprising a forward and a reverse primer for amplifying the genomic DNA region, wherein each primer of the primer pair comprises a template-specific portion hybridizing to a portion of said sequence of the genomic DNA region and a second portion that is a universal sequence.

8. The method according to claim 7, wherein the primer pairs of step (iv) are selected from:
  SEQ ID NOs: 1 and 2 and/or SEQ ID NOs: 27 and 28 for amplifying PARP15; and/or
  SEQ ID NOs: 3 and 4 and/or SEQ ID NOs: 29 and 30 for amplifying ITGA4; and/or
  SEQ ID NOs: 5 and 6 and/or SEQ ID NOs: 31 and 32 for amplifying NMT; and/or
  SEQ ID NOs: 7 and 8 and/or SEQ ID NOs: 33 and 34 for amplifying ZAP70; and/or
  SEQ ID NOs: 9 and 10 and/or SEQ ID NOs: 35 and 36 for amplifying MIR193A; and/or
  SEQ ID NOs: 11 and 12 and/or SEQ ID NOs: 37 and 38 for amplifying EPKH3; and/or
  SEQ ID NOs: 13 and 14 and/or SEQ ID NOs: 39 and 40 for amplifying KIF1A; and/or
  SEQ ID NOs: 15 and 16 and/or SEQ ID NOs: 41 and 42 for amplifying LINC00599; and/or
  SEQ ID NOs: 17 and 18 and/or SEQ ID NOs: 43 and 44 for amplifying FLI1; and/or
  SEQ ID NOs: 19 and 20 and/or SEQ ID NOs NG: 45 and 46 for amplifying GP1BB; and/or
  SEQ ID NOs: 21 and 22 and/or SEQ ID NOs: 47 and 48 for amplifying MIR296 and/or SEQ ID NOs: 23 and 24 and/or SEQ ID NOs: 49 and 50 for amplifying LRRTM1; and/or SEQ ID NOs: 25 and 26 and/or SEQ ID NOs NG: 51 and 52 for amplifying human TERT.

9. The method according to claim 5, wherein the second amplification step involves using primer pairs, said primer pairs comprising a forward and a reverse primer, wherein each primer of the primer pairs comprises, starting from the 5' end of the primer sequence: 1) an adaptor sequence specific for a sequencing platform to be used; 2) a sample-specific barcode sequence; and 3) a universal linker tag corresponding to a universal sequence of the primer pairs used in the first amplification step.

10. The method according to claim 1, wherein after the amplification step (iv), the amplified sequences are sequenced by using a next-generation sequencing (NGS) platform.

11. The method according to claim 1, wherein a multiclass Linear Discriminant Analysis is used to measure the total methylation level of the CpG/CpG islands of at least one genomic DNA region of more than one gene of interest.

12. The method according to claim 11, wherein after the Linear Discriminant Analysis a ROC curve is obtained to define a threshold able to determine a HNSCC-positive sample.

13. The method according to claim 12, wherein said positive sample is OSCC or HG-SIL.

14. The method according to claim 1, wherein in said step (iii) the genomic DNA is treated with sodium bisulfite.

\* \* \* \* \*